US011065388B2

(12) United States Patent
Cowe et al.

(10) Patent No.: US 11,065,388 B2
(45) Date of Patent: Jul. 20, 2021

(54) MEDICAMENT PACKAGING

(71) Applicant: Owen Mumford Limited, Oxfordshire (GB)

(72) Inventors: Toby Cowe, Oxfordshire (GB); Timothy Evans, Oxfordshire (GB); Colin Webb, Oxfordshire (GB); Jake Mallon, Oxfordshire (GB)

(73) Assignee: Owen Mumford Limited, Oxford (GB)

( * ) Notice: Subject to any disclaimer, the term of this patent is extended or adjusted under 35 U.S.C. 154(b) by 740 days.

(21) Appl. No.: 15/739,449

(22) PCT Filed: Jul. 13, 2016

(86) PCT No.: PCT/GB2016/052114
§ 371 (c)(1),
(2) Date: Dec. 22, 2017

(87) PCT Pub. No.: WO2017/009640
PCT Pub. Date: Jan. 19, 2017

(65) Prior Publication Data
US 2018/0185584 A1 Jul. 5, 2018

(30) Foreign Application Priority Data

Jul. 13, 2015 (GB) ..................................... 1512222

(51) Int. Cl.
*A61M 5/24* (2006.01)

(52) U.S. Cl.
CPC ............ *A61M 5/2455* (2013.01); *A61M 5/24* (2013.01); *A61M 2005/2403* (2013.01); *A61M 2005/247* (2013.01); *A61M 2005/2407* (2013.01)

(58) Field of Classification Search
CPC .................. A61M 5/2455; A61M 5/24; A61M 2005/2403; A61M 2005/2407; A61M 2005/247
See application file for complete search history.

(56) References Cited

U.S. PATENT DOCUMENTS 4,445,895 A 5/1984 Margulies
4,553,962 A * 11/1985 Brunet ................ A61M 5/2033
604/198

(Continued)

FOREIGN PATENT DOCUMENTS

| GB | 1181037 | 2/1970 |
| WO | WO 2006/058435 A2 | 6/2006 |
| WO | WO 2009/137486 A1 | 11/2009 |

OTHER PUBLICATIONS

Nov. 18, 2016 Transmittal of International Search Report and Written Opinion of International Searching Authority for PCT/GB2016/052114.

*Primary Examiner* — Lauren P Farrar
(74) *Attorney, Agent, or Firm* — Quarles & Brady LLP

(57) ABSTRACT

A cartridge (100) for packaging a medicament and being suitable for use with multiple different types of dosing device is described, together with dosing devices and adaptors for dosing devices. The cartridge includes a generally tubular body (102) having an interior cavity (104), a closure member (106) disposed at a distal end of the body and comprising a sealing element (128), a piston member (108) disposed in the cavity to contain the medicament between the piston member and the sealing element (128), a coupling element (114) disposed at the distal end of the body for coupling the cartridge to a dosing device (200) or to an adaptor for a dosing device, and a seal arrangement (126, 129) for receiving a sealing element release member (214) of the dosing device or adaptor. The coupling element (114)

(Continued)

is arranged for engagement with an engagement part (220) of the dosing device or adaptor to clip the cartridge (100) to the dosing device or adaptor (200) upon insertion of the cartridge to the dosing device or adaptor, and the seal arrangement (126, 129) is disposed distally with respect to the sealing element (128) and is arranged to form a seal around the release member (214; 254) when the cartridge is coupled to the dosing device or adaptor.

38 Claims, 15 Drawing Sheets

(56) References Cited

U.S. PATENT DOCUMENTS

| | | |
|---|---|---|
| 5,554,134 A | 9/1996 | Bonnichsen |
| 6,126,646 A | 10/2000 | Hansen et al. |
| 2006/0178638 A1* | 8/2006 | Reynolds ............ A61M 5/2448 604/191 |
| 2011/0092917 A1* | 4/2011 | Wei ........................ A61M 5/24 604/241 |
| 2012/0203185 A1 | 8/2012 | Kristensen et al. |
| 2013/0158500 A1 | 6/2013 | Woolston |
| 2013/0204201 A1 | 8/2013 | Avery et al. |
| 2013/0253432 A1 | 9/2013 | Avery et al. |
| 2013/0289488 A1 | 10/2013 | Riess et al. |
| 2015/0073353 A1 | 3/2015 | Strader |

\* cited by examiner

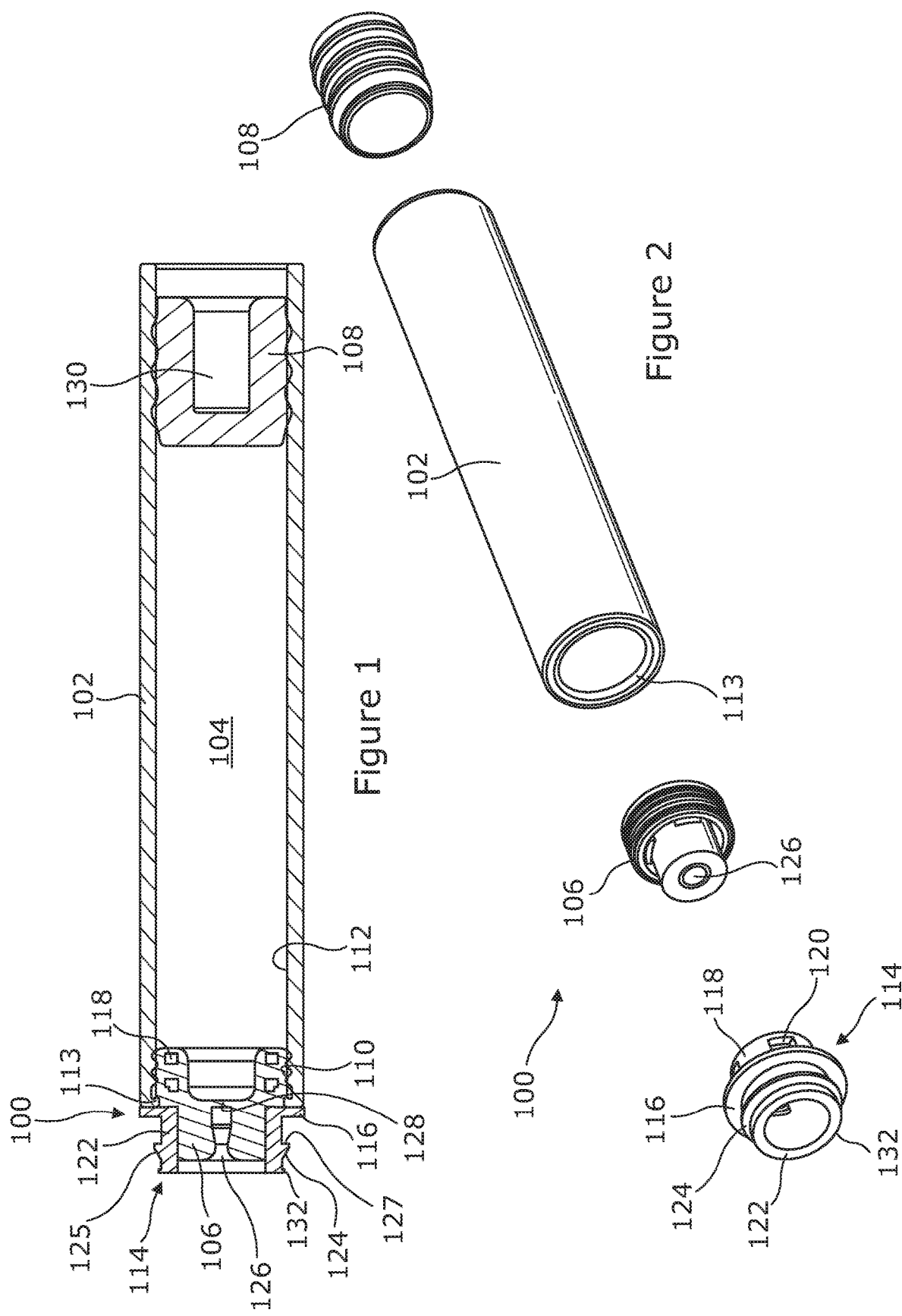

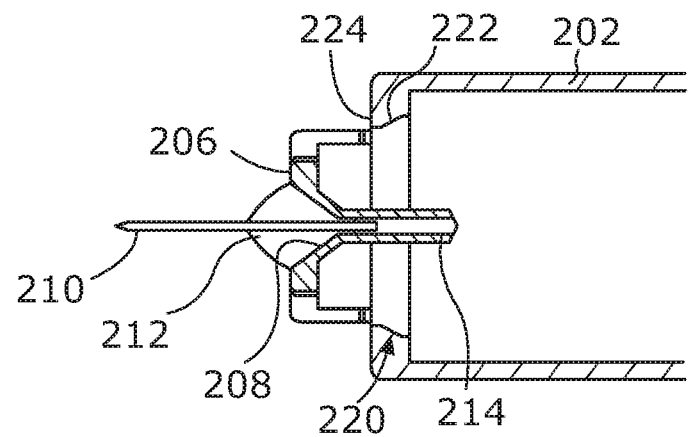
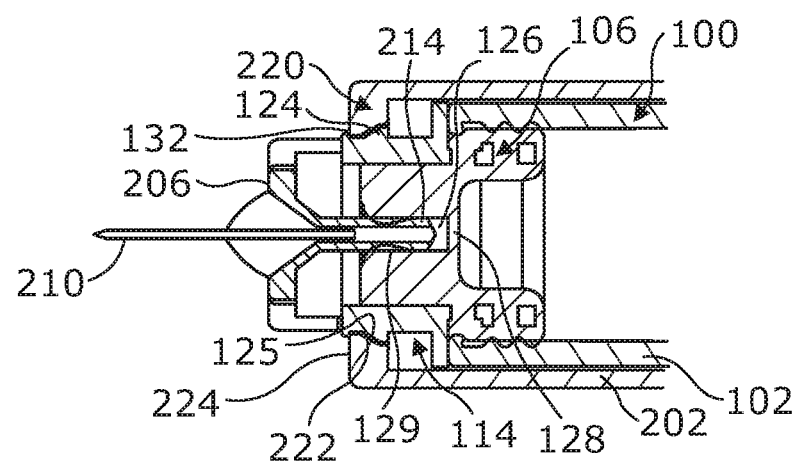
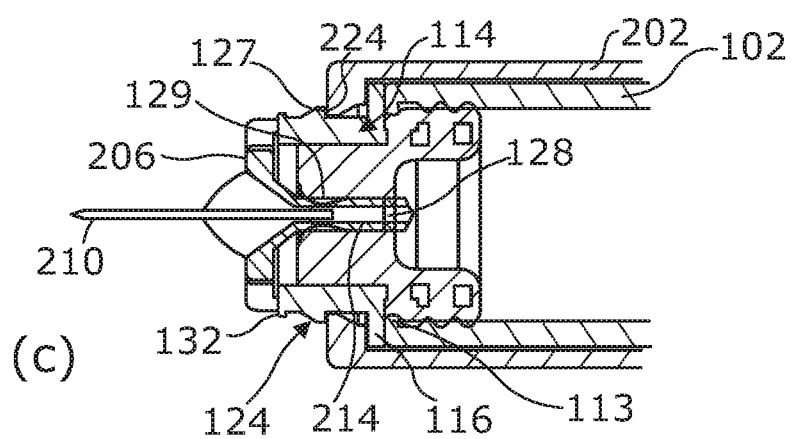
Figure 4

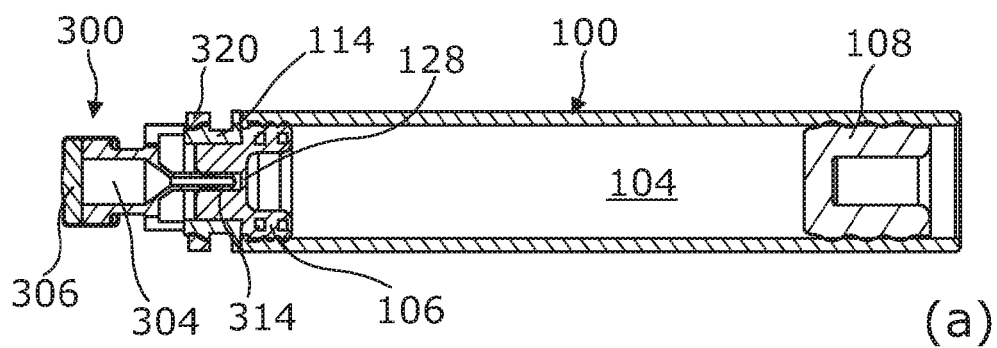
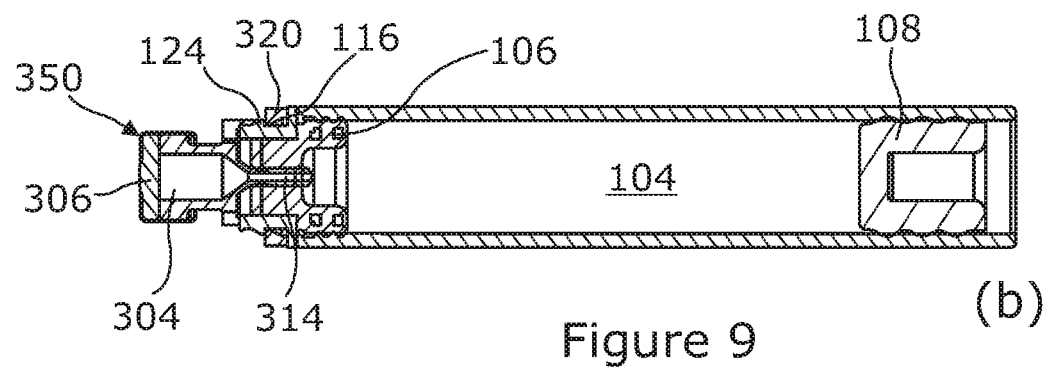
Figure 9

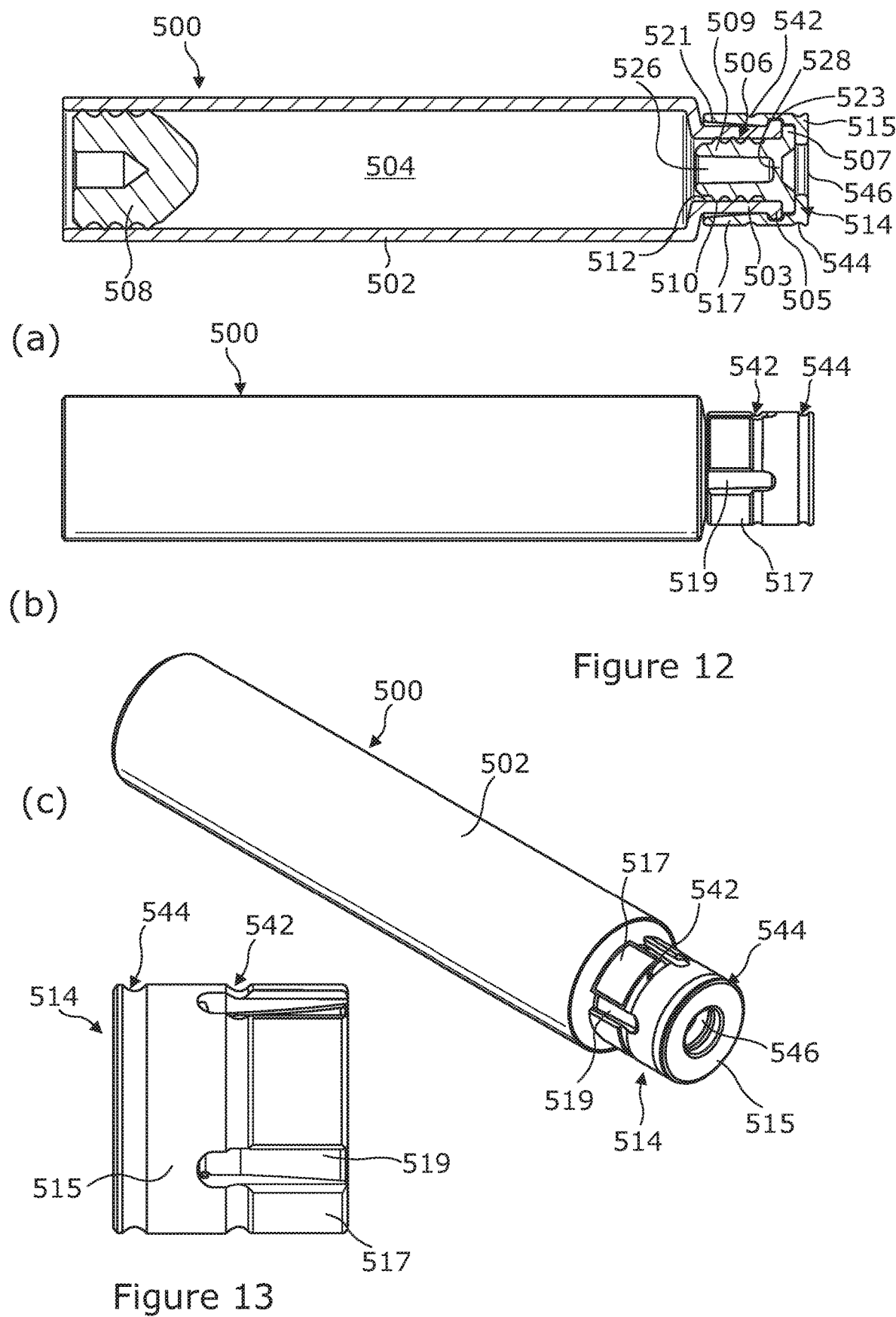

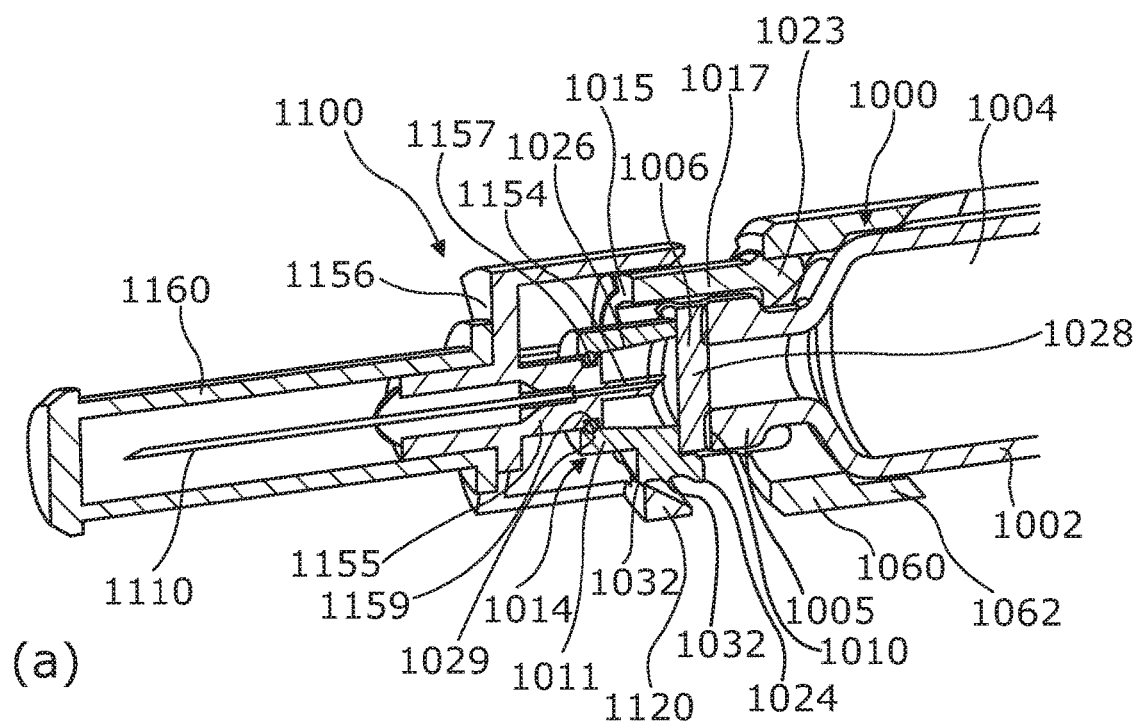
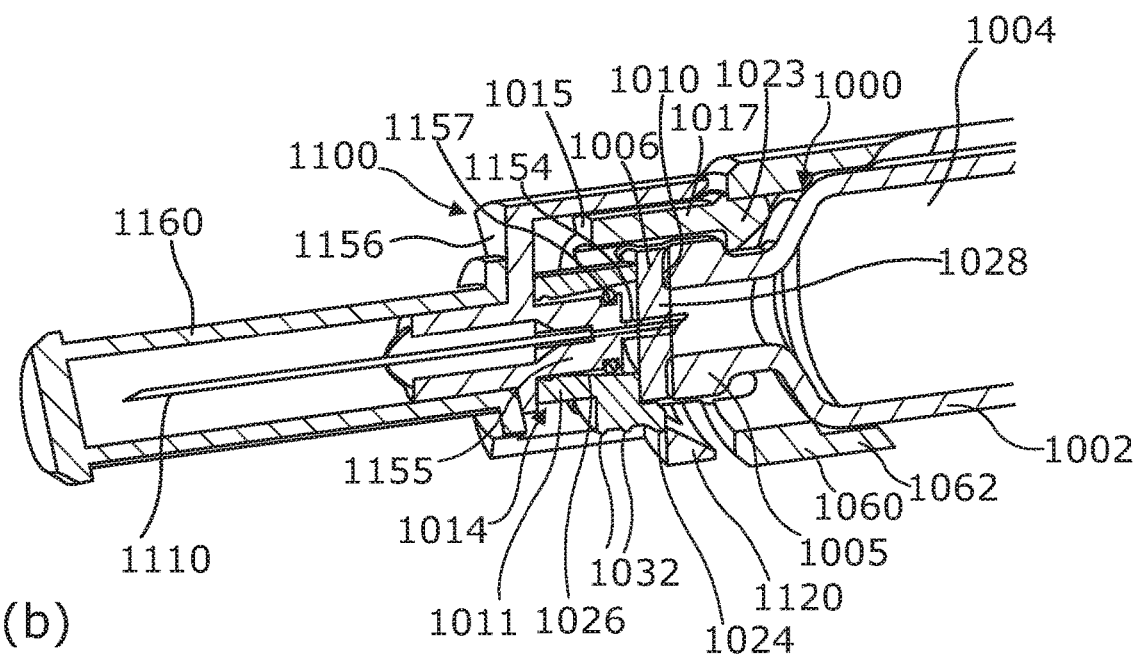
Figure 17

MEDICAMENT PACKAGING

The present application is a US national stage of international application no. PCT/GB2016/052114, filed 13 Jul. 2016 and entitled Medicament Packaging, which was published in the English language on 19 Jan. 2017 with publication no. WO2017/009640 A1, and which claims the benefit of the filing date of GB 1512222.9 filed 13 Jul. 2015, the contents of which are incorporated herein by reference.

This invention relates to packaging for medicaments. In particular, but not exclusively, the invention relates to cartridge-type primary packaging for injectable or infusable medicaments and adaptors and devices for use with the primary packaging.

Medicaments for subcutaneous injection are used in therapy in various different clinical situations, and a corresponding variety of injection devices have been developed to suit each situation.

For example, injectable medicaments may be supplied in traditional vials for use with a separate syringe. Such vials may be closed with a polymeric membrane or septum that can be pierced by a syringe needle, allowing the medicament to be drawn into the syringe. The septum is typically self-sealing to prevent leakage of the medicament once the needle is withdrawn.

Another approach is to provide a pre-filled, disposable syringe containing a single dose of the medicament. In this case, the medicament is contained in a tubular syringe body by a slidable stopper. In one common staked-needle design, sold under the registered trade mark Hypak (Becton Dickinson, New Jersey, USA), the needle is permanently fixed to the distal end of the syringe body. In other designs, the syringe body may be configured to accept a removable needle, for instance with a luer-type fitting. A plunger protrudes from a proximal end of the syringe body to allow the stopper to be displaced for delivery of the medicament through the needle. These disposable devices are relatively inexpensive and are often more convenient than a traditional syringe and vial for delivery of a fixed dose of medicament but, like the syringe and vial, they are generally suitable for use only by trained individuals with a reasonable degree of manual dexterity.

Accordingly, more sophisticated injection devices have been developed for use in situations where some degree of automation of the injection process is desired and/or where the use of a traditional syringe or pre-filled syringe would be difficult or inconvenient. Examples include the self-administration of medicaments by patients and emergency treatment by untrained personnel.

For example, injection devices known as auto-injectors are generally intended for the administration of a single, fixed dose of medicament. Typically, in such devices, one or more of needle insertion, medicament delivery, dose indication, needle retraction and deployment of a needle shield after injection are triggered by one or more user operations, such as operating a trigger button or slider.

The medicament dose in an auto-injector is usually provided in the form of a disposable, pre-filled glass syringe with a fixed needle, such as a Hypak syringe of the type described above. Auto-injector mechanisms typically include a mechanically-driven plunger to drive the stopper of the syringe, and may be arranged to move the syringe body with respect to a body of the auto-injector to effect insertion and/or retraction of the needle. In many cases, the auto-injector is not re-usable and the pre-filled syringe cannot be replaced. Instead, when the medicament has been delivered, the auto-injector is discarded along with the pre-filled syringe within.

Other injection devices, sometimes known as injection pens, contain multiple doses of a medicament and are intended to be re-used. Re-usable devices are invariably designed for use with disposable, single-use double-ended needles, which are interchangeable to allow a fresh, sterile needle to be fitted for each injection. Such devices often include a mechanism for adjusting the amount of medicament to be delivered with each injection, and may incorporate a trigger mechanism to deliver automatically the required dose upon activation of a trigger button. Injection pen devices are routinely used for self-administration of, for example, insulin and human growth hormone.

In an injection pen, the medicament is typically packaged in a pre-filled cartridge. The medicament is contained between a self-sealing polymeric membrane or septum at the distal end of the cartridge, and a slidable stopper that can be driven by a plunger of the injection pen. The septum is pierced by the inside end of the needle when the needle is fitted to the device and, upon removal of the needle, the septum re-seals to prevent leakage of the medicament.

In some cases, the distal end of the cartridge includes a fitting that protrudes from the distal end of the injection pen device, and the needle engages directly with the cartridge. In other designs, the needle engages with the body of the injection pen device, rather than the cartridge itself. Most commonly, injection pen devices use screw-fit needles, although other needle designs, such as bayonet fittings and clip fittings, are also known.

Some injection pen devices employ replaceable cartridges, which allow the device to be refilled once each cartridge is empty. In other cases, the medicament cartridge is not replaceable, and the device is discarded when the medicament has been exhausted.

In some therapies, the administration of medicaments by infusion over a relatively long time period is preferred. One increasingly common example is the use of insulin pumps for the treatment of diabetes mellitus. In such cases, the medicament is typically packaged in a reservoir. The reservoir includes a slidable stopper that can be driven by a plunger mechanism in the pump, and a fitting to allow connection to a cannula. The fitting may include a luer-type or proprietary connection, and the cannula may be connected to the reservoir either by way of a flexible tube or, in so-called "patch pump" designs, directly or through a rigid connection. Some pump designs use refillable reservoirs, in which case the medicament may be supplied in a vial with a corresponding fitting to allow secure attachment of the pump reservoir during refilling. Other pump devices use pre-filled, cartridge-type reservoirs which are exchanged when empty.

It will be appreciated that, in all of these examples, the design of the primary packaging (i.e. the type of container in which a medicament is initially supplied from the manufacturer) is of key importance in the successful and safe operation of the injection or infusion device.

To ensure compatibility and safety of primary packages, it is necessary to test and validate every combination of medicament and primary packaging that is released to the market. The validation process may involve clinical trials and regulatory approval, and may therefore be extremely expensive and time-consuming.

As a result, many medicaments are currently available in only one or two different primary packages, reducing the choice of device available for administration of that medicament. In some cases, the cost of validating a new primary package for an existing medicament may be prohibitive. In other cases, where a new dedicated primary package for a new device is developed, the increased medicament cost may discourage the approval of new devices by healthcare funding bodies or insurers. Conversely, when designing new delivery devices for established medicaments, aspects of the design may be undesirably restricted by the type of primary packaging already available for the particular medicament in question.

Accordingly, it would be desirable to provide primary packaging for medicaments that has improved compatibility with different delivery devices.

Against this background, and from a first aspect, the present invention resides in a cartridge for packaging a medicament, which is suitable for use with multiple different types of dosing device. The cartridge comprises a generally tubular body having an interior cavity, a closure member disposed at a distal end of the body and comprising a sealing element, a piston member disposed in the cavity to contain the medicament between the piston member and the sealing element, a coupling element disposed at the distal end of the body for coupling the cartridge to a dosing device or to an adaptor for a dosing device, and a seal arrangement for receiving a sealing element release member of the dosing device or adaptor. The coupling element is arranged for engagement with an engagement part of the dosing device or adaptor to clip the cartridge to the dosing device or adaptor upon insertion of the cartridge to the dosing device or adaptor, and the seal arrangement is disposed distally with respect to the sealing element and is arranged to form a seal around the release member when the cartridge is coupled to the dosing device or adaptor.

The coupling element is configured to allow the cartridge to be clipped to a suitable dosing device or adaptor provided with a corresponding engagement part. In this way, the cartridge of the present invention provides primary packaging for a medicament that can be used with multiple different types of dosing device, either directly when the dosing device is configured to engage with the cartridge, or by way of a suitable adaptor. Advantageously, therefore, medicament can be supplied by a manufacturer in a single primary package type.

The term "dosing device" includes any device, apparatus or assembly that can be fitted to the cartridge for delivery of medicament from the cartridge. For example, the cartridge can be used with dosing devices including reusable injection pens, auto-injectors, disposable syringes and infusion pumps (including remote pumps and patch-style pumps). The cartridge can similarly be fitted with a dosing device in the form of a needle assembly, a cannula connector, an infusion line connector and so on. The cartridge can also be used with adaptors that adapt the cartridge for use in dosing devices, such as injection pens, that are compatible with cartridges of a different, non-universal design, or that adapt the cartridge for use as a vial for filling a syringe or another device.

Because a single cartridge design can be used with multiple devices, the requirement to validate multiple medicament packages for supply of a particular medicament can be avoided. Furthermore, the cost of supplying medicament in a single package type is lower than the cost of supplying multiple packages for specific applications. Also, the cartridge can be used in many different clinical situations and with many different types of dosing device, improving patient and clinician choice when selecting a suitable method of administering a medicament.

Furthermore, the inclusion of a seal arrangement that receives and forms a seal around a release member of the dosing device or adaptor allows the sterility of the release member to be maintained by the cartridge. Because the seal arrangement is distally with respect to the sealing element, the seal around the release member may be established before the release member cooperates with the sealing element to release the medicament. Thus the cartridge can be pre-assembled with a dosing device or adaptor for supply to a user with minimum risk of compromising the sterility of any medicament-contacting parts of the container or the device. To that end, the seal arrangement may provide an enclosed chamber adjacent the sealing element for receiving a proximal tip of the release member when the seal is formed around the release member.

The coupling element may be arranged to define first and second insertion positions for the cartridge with respect to the dosing device or adaptor. The sealing element may be positioned such that, when the cartridge is in the first insertion position, the sealing element prevents release of the medicament from the cartridge, and when the cartridge is in the second insertion position, the sealing element cooperates with the release member of the dosing device or adaptor to allow flow of the medicament from the cartridge. Accordingly, the cartridge can be placed into engagement with the dosing device or adaptor in the first insertion position without releasing the medicament from the cartridge, for example for transport and storage and to preserve the sterility and integrity of the medicament. When administration of the medicament is required, the cartridge can be moved into the second insertion position to release the medicament through the sealing element.

Preferably, the seal arrangement is arranged to form a seal around the release member when the cartridge is in the first insertion position, to preserve the sterility of the release member. The seal may be maintained when the cartridge is moved to the second insertion position or, alternatively, the seal may be released when the cartridge is moved to the second insertion position.

The seal arrangement may comprise a passage for receiving the release member, and the sealing element may close the passage. An inner wall of the passage may comprise a sealing surface arranged to form the seal around the release member. The sealing surface may, for example, be defined by a narrowed region of the passage. In one embodiment, an inner wall of the passage is resilient to form a seal against an outer surface of the release member when the release member is received in the passage. The passage may have a smaller internal diameter than an external diameter of the release member.

In another example, the inner wall of the passage comprises a recess for receiving a sealing ring to form the seal around the release member. The sealing ring, which may comprise an elastomeric O-ring, may be retained by the cartridge or by the dosing device or adaptor.

The closure member may comprise the seal arrangement. For instance, the closure member may be elastically deformable to receive the release member and to form the seal around the release member. In one embodiment, the closure member comprises a bore that forms the passage of the seal arrangement.

The coupling element is preferably a polymeric moulding, for example of a rigid plastics material. The closure member is preferably of an elastomeric material.

The closure member may comprise an elastomeric bung that is at least partially received in the distal end of the cavity of the body. An outer surface of the bung may form an annular seal with an inner surface of the body. In this way, a crimped metal end fitting for retaining the closure member, as used in some conventional cartridges, is not necessary. The body may comprise an internal lip for retaining the bung in the body. Alternatively, or in addition, the bung may be retained in the body by a frictional fit between the outer surface of the bung and the inner surface of the body.

The coupling element may be attached to the bung to secure the coupling element to the body. For example, the coupling element may include a skirt that extends into the cavity, and the bung may be overmoulded over the skirt to attach the coupling element to the bung. Alternatively, or in addition, the coupling element may be otherwise mechanically or adhesively attached to the bung. By securing the coupling element to the body by way of attachment to the bung, rather than by engagement with a collar or neck of the body, the shape of the body need be less complex. For example, the body may be a tube with a straight-sided outer surface.

In another arrangement, the coupling element comprises the seal arrangement. In one example, the seal arrangement comprises a tubular portion or throat for receiving the release member. A proximal end of the tubular portion may be arranged to clamp the closure member to the body.

When the coupling element comprises the seal arrangement, the closure member can have a simple form. For example, the closure member may be an elastomeric disc. Thus the closure member may be of the type used in medicament cartridges having a crimped end fitting as known in the prior art. Because the closure member can be retained in position against the body by the coupling element, a crimped end fitting is not required. However, in some arrangements, a crimped end fitting may be provided, and the coupling element may seal against the end fitting.

In such arrangements, the coupling element may be arranged to cooperate directly with the body to attach the coupling element to the body. For example, the distal end of the body may comprise an annular collar, and the coupling element may include a clip formation to engage with the collar, thereby to secure the coupling element to the body. The collar is preferably disposed on a reduced-diameter distal portion of the body. The clip formation may comprise a ramped proximal face to allow the clip formation to be pushed over the collar during assembly of the cartridge. A plurality of clip formations may be provided.

The coupling element may be arranged to apply a clamping force to the closure member when the clip formation is engaged with the collar, thereby to retain the closure member against the body. The cartridge may comprise a retainer for applying a retaining force to the clip formation to maintain engagement between the clip formation and the collar. In this way, the retainer prevents the coupling element from becoming unintentionally separated from the body. The retainer may, for example, comprise a band or ring arranged concentrically around the coupling element and the collar of the body. The retainer may be part of a sleeve or housing for the body.

The coupling element may comprise a flange that abuts the distal end of the body. The coupling element may comprise a sleeve or nose that extends distally from the flange. The sleeve may be configured for insertion into a receiving part of the dosing device or adaptor. When provided, the engagement formation may be disposed on the sleeve of the coupling element. In another arrangement, the coupling element comprises an annular body, and the engagement formation is disposed on the annular body. The engagement formation may be disposed in a recess formed in the outer wall of the annular body, in which case the recess may be shaped to guide the engagement part of the dosing device or the adaptor into engagement with the engagement formation.

The coupling element may comprise an engagement formation for cooperation with the engagement part of the dosing device or adaptor. In one embodiment, the engagement formation comprises a ramp formation for cooperation with the engagement part of the dosing device or adaptor. The ramp formation may be configured to engage with the engagement part of the dosing device or adaptor upon insertion of the cartridge. The ramp formation may comprise a ramped distal side to allow the ramp formation to pass the engagement part upon insertion of the cartridge in a distal direction. In this way, the cartridge is guided into engagement with the dosing device or adaptor upon insertion. The ramp formation may have a perpendicular proximal side to restrict movement of the cartridge in a proximal direction after insertion of the cartridge, thereby preventing the cartridge from detaching from the dosing device or adaptor after the cartridge has been clipped to the dosing device or adaptor. The ramp formation may comprise an annular projection on the coupling element. Alternatively, the ramp formation may be disposed on a proximally-extending leg of the coupling element.

In another embodiment, the engagement formation comprises a recess for engagement with a corresponding projection of the dosing device or adaptor. For example, the recess may comprise an annular channel in the coupling element.

When the coupling element is arranged to define first and second insertion positions for the cartridge with respect to the dosing device or adaptor, the coupling element may comprise first and second engagement formations for cooperation with the dosing device or adaptor thereby to define the first and second insertion positions. The first and second engagement formations may cooperate with the same engagement part of the dosing device or adaptor, or with respective first and second engagement parts of the dosing device or adaptor.

The sealing element is preferably formed integrally with the closure member. Alternatively, the sealing element may be a separate component, in which case the closure member may comprise a support part and the sealing element part. The sealing element may comprise a pierceable septum, a valve component, or any other suitable structure for sealing the medicament in the cartridge.

A second aspect of the invention resides in a cartridge connector for a dosing device or adaptor for use with the cartridge of the first aspect of the invention. The cartridge connector comprises an engagement part configured to engage with the coupling element of the cartridge to clip the cartridge to the dosing device or adaptor upon insertion of the cartridge to the cartridge connector.

The engagement part of the cartridge connector may be configured to engage with an engagement formation of the coupling element of the cartridge. The engagement part may, for example, comprise one or more clips, one or more projections, one or more recesses, or any combination of such features suitable for engagement with the engagement formation of the cartridge. In one example, the engagement part comprises a ramp formation for cooperation with the engagement formation of the coupling element of the cartridge. The ramp formation may include a ramped proximal side to allow the engagement formation on the coupling element of the cartridge to pass the ramp formation upon insertion of the cartridge. The ramp formation may comprise a perpendicular distal side for engagement with the engagement formation, thereby to restrict movement of the cartridge in a proximal direction after insertion of the cartridge.

In a third aspect of the invention, a dosing device comprising a cartridge connector according to the second aspect of the invention is provided. The dosing device may, for example, comprise an auto-injector, an injection pen, a disposable syringe device, a needle assembly, a cannula connector, a medicament pump, a patch pump or an infusion patch.

The dosing device may comprise a sealing element release member arranged to cooperate with the sealing element of the closure member upon insertion of the cartridge to allow release of medicament from the cartridge.

In some cases, such as when the dosing device is an injection pen, the device may be arranged to accept a replaceable single-use double-ended hypodermic needle that pierces the sealing element of the cartridge when the needle is fitted to the device, such that a proximal end of the needle provides the release member.

In other examples, such as when the dosing device comprises an auto-injector, a disposable syringe device, a needle assembly, an infusion patch or a pump, the dosing device may comprise a cannula, such as a needle, and the release member may be in fluid connection with the cannula. In other words, the release member and the cannula may be separate components. In one example, the release member comprises a tube member in fluid connection with the cannula. A proximal end of the tube member may be pointed to pierce the sealing element.

In such cases, the seal arrangement may be arranged to form a seal directly against the tube member, or the seal arrangement may be arranged to form a seal against another component of the release member. For example, the tube member may extend from an enlarged diameter part or hub part of the release member, and the seal arrangement may be arranged to form a seal with the enlarged diameter part of the release member.

In other arrangements, the release member may comprise a proximal end of a hypodermic needle (i.e. the hypodermic needle acts also as the release member).

When the release member and the cannula are separate components, the cannula may be non-axially aligned with respect to the release member. For example, the cannula may be approximately perpendicular to the release member. The cannula may be moveable with respect to a body of the dosing device to allow transdermal insertion of the needle. Such arrangements are particularly useful when the dosing device comprises an infusion patch, patch pump or other wearable device.

A fourth aspect of the present invention provides an injection device for injecting a medicament. The injection device includes a housing having an engagement part and a hypodermic needle, and a medicament cartridge having a generally tubular body defining an interior cavity, a closure member disposed at a distal end of the body and having a sealing element, a piston member disposed in the cavity to contain the medicament between the piston member and the sealing element, and a coupling element disposed at the distal end of the body. The coupling element is engaged or engageable with the engagement part to clip the cartridge to the housing. The medicament cartridge may be in accordance with the first aspect of the invention. In one example, the injection device of this fourth aspect of the invention is a disposable syringe device intended for single use.

Preferably, when the coupling element is engaged with the engagement part, the housing shrouds the cartridge to guard against removal of the cartridge. This helps to discourage tampering with the device.

The injection device may further comprise a release member arranged to cooperate with the sealing element to allow release of medicament from the cartridge. In one example, the release member comprises a proximal end of the needle. Alternatively, the release member may comprise a tubular member that may be integrally formed with the housing.

Dosing devices and injection devices according to aspects of the invention may further comprise a plunger which is attached or attachable to the piston member. The plunger may be intended for manual use, in which case a housing of the device may comprise finger tabs to aid manual depression of the plunger. In other cases, the plunger may be mechanically driven by a drive mechanism of the device.

It may be desirable to use the cartridge of the first aspect of the invention in injection pens, pumps and other devices of conventional, existing designs, which do not include engagement parts that are specifically configured to clip to the cartridge.

Accordingly, in a fifth aspect, the present invention extends to an adaptor for use with a cartridge according to the first aspect of the invention and is configured to adapt the cartridge for use with a dosing device, for example of a conventional design.

The adaptor comprises an engagement part, an adaptor body housing a medicament chamber, and an adaptor seal for sealing a distal end of the chamber, wherein the engagement part is arranged to engage with the coupling element of the cartridge to clip the cartridge to the adaptor. The engagement part may be arranged to receive the coupling element of the cartridge.

The adaptor may further comprise a sealing element release member, and the release member may be arranged to cooperate with the sealing element of the cartridge to allow flow of medicament from the cartridge to the chamber when the cartridge is clipped to the adaptor. The sealing element of the cartridge may comprise a pierceable septum, and the release member may comprise a tubular piercing member fluidly connected to the chamber. In alternative arrangements, the sealing element may comprise a valve, and the release member may comprise a valve opening member arranged to open the valve upon cooperation therewith.

The adaptor may comprise a cap fitting for securing the adaptor seal to the adaptor body. For example, the cap fitting may comprise a crimp closure and the adaptor body may comprise a lip for retaining the closure. The adaptor seal may be a self-sealing septum.

To adapt the cartridge for use in a particular dosing device, at least part of the adaptor body may have an outer diameter that differs from the outer diameter of the coupling element of the cartridge. In particular, the adaptor body may be dimensioned for compatibility with a medicament dosing device. For example, the adaptor body may have an outer diameter that is smaller than the outer diameter of the coupling element of the cartridge, and that matches the outer diameter of a distal part of the conventional cartridge usually used in the device.

The adaptor may include attachment means for attachment of a disposable needle to the adaptor. The attachment means may comprise, for example, screw threads. In this way, the adaptor allows the cartridge of the first aspect of the invention to be used in dosing devices in which the needle mounts directly to a conventional cartridge. Alternatively, when the needle mounts to the dosing device, the adaptor may have a plain body without needle attachment means.

In further aspects, the invention also extends to a medicament cartridge assembly comprising an adaptor according to the fifth aspect of the invention fitted to a medicament cartridge according to the first aspect of the invention, and to an injection pen comprising a medicament cartridge assembly of this type.

In another aspect, the present invention resides in a cartridge for packaging a medicament, which is suitable for use with multiple different types of dosing device. The cartridge comprises a generally tubular body having an interior cavity, a closure member disposed at a distal end of the body and comprising a sealing element, a piston member disposed in the cavity to contain the medicament between the piston member and the sealing element, and a coupling element for coupling the cartridge to a dosing device or to an adaptor for a dosing device. The coupling element is disposed at the distal end of the body, and comprises an engagement formation for engagement with a corresponding engagement part of the dosing device or adaptor to clip the cartridge to the dosing device or adaptor upon insertion of the cartridge to the dosing device or adaptor. In this aspect, the provision of a seal arrangement for forming a seal around a sealing element release member of the dosing device or adaptor is optional.

In a further aspect, the present invention resides in a cartridge for packaging a medicament, which is suitable for use with multiple different types of dosing device. The cartridge comprises a generally tubular body having an interior cavity, a closure member disposed at a distal end of the body and comprising a sealing element, a piston member disposed in the cavity to contain the medicament between the piston member and the sealing element, and a coupling element for coupling the cartridge to a dosing device or to an adaptor for a dosing device. The coupling element is disposed at the distal end of the body. The cartridge further comprises a seal arrangement for forming a seal with the dosing device or adaptor to provide an enclosed chamber adjacent the sealing element for receiving a proximal tip of a sealing element release member of the dosing device or adaptor.

The cartridge and/or the dosing device or adaptor may be arranged to define first and second insertion positions for the cartridge with respect to the dosing device or adaptor. In the first insertion position, the sealing element may prevent release of the medicament from the cartridge, and in the second position, the sealing element release member may cooperate with the sealing element to allow flow of the medicament from the cartridge. In this case, the seal arrangement may form a seal with the dosing device or adaptor at least when the cartridge is in the first insertion position.

The coupling element may comprise the seal arrangement. The seal arrangement may be arranged to form a seal with an inside or internal wall of the dosing device or adaptor. For example, the seal arrangement may be arranged to form a seal against the inside wall of a tubular socket or other tubular part or cylindrical recess of the dosing device or adaptor. In another example, the seal may be formed around an outer diameter associated with the sealing element release member. The seal formed by the seal arrangement may be disposed distally or proximally with respect to the sealing element, or may be substantially alongside the sealing element.

Preferred and/or optional features of each aspect of the invention may be used, alone or in appropriate combination, with the other aspects of the invention also.

Embodiments of the present invention will now be described, by way of example only, with reference to the accompanying drawings, in which like reference numerals are used for like features, and in which:

FIG. 1 is a cross-sectional view of a medicament package;

FIG. 2 is an exploded isometric view of the medicament package of FIG. 1;

FIG. 4 shows cross-sectional views of part of the syringe device of FIG. 3 before insertion of the medicament package (FIG. 4(a)), and with the medicament package at a first insertion position (FIG. 4(b)) and at a second insertion position (FIG. 4(c));

FIG. 9 shows cross-sectional views of the adaptor device of FIG. 7 with the medicament package in a first insertion position (FIG. 9(a)) and in a second insertion position (FIG. 9(b));

FIG. 12 shows another medicament package in cross-sectional, side and isometric views;

FIG. 13 is a side view of a coupling element of the medicament package of FIG. 12;

FIG. 17 shows cut-away isometric views of another medicament package in use with another dosing device, with the medicament package partially inserted (FIG. 17(a)) and fully inserted (FIG. 17(b));

Figure 18:
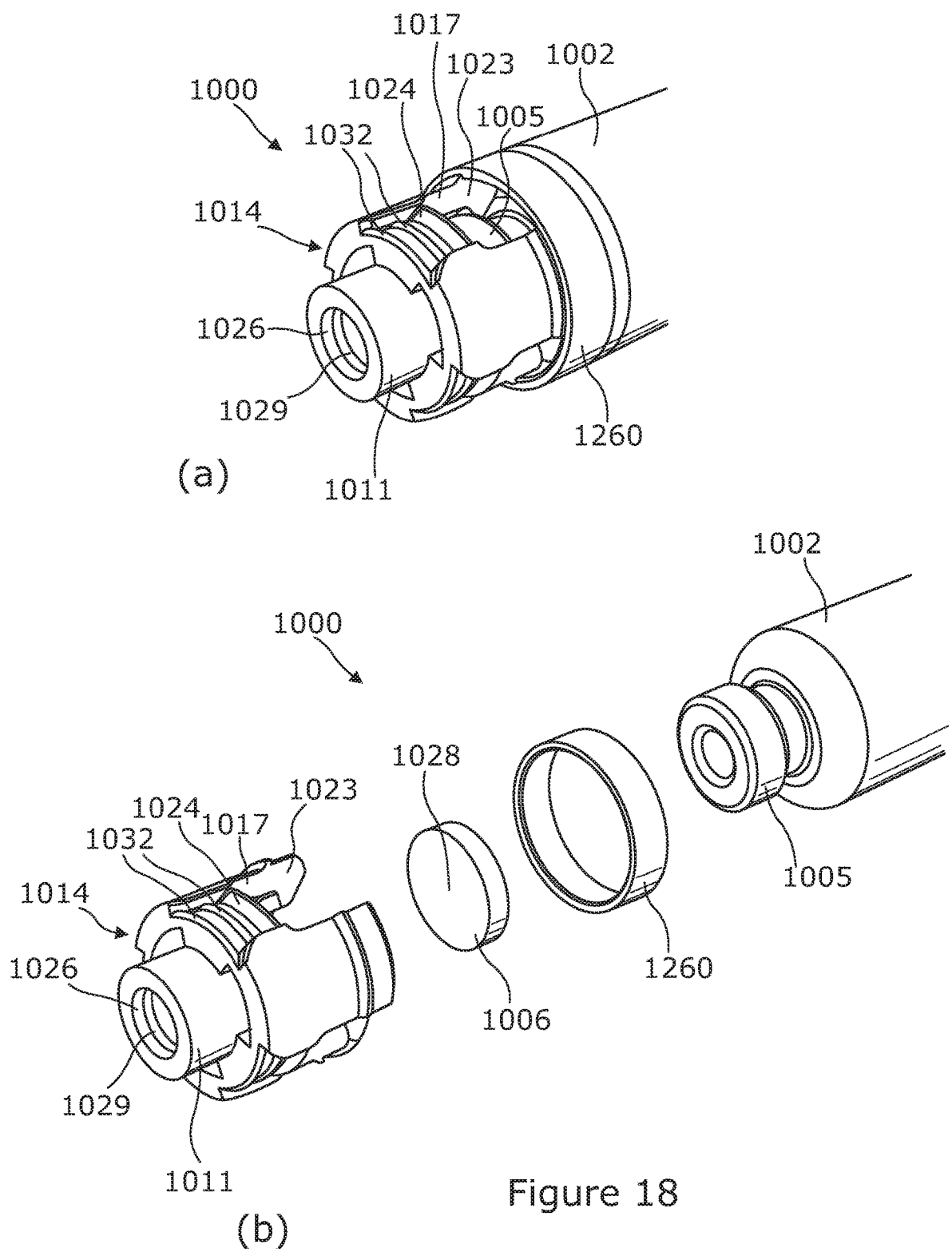
Figure 19:
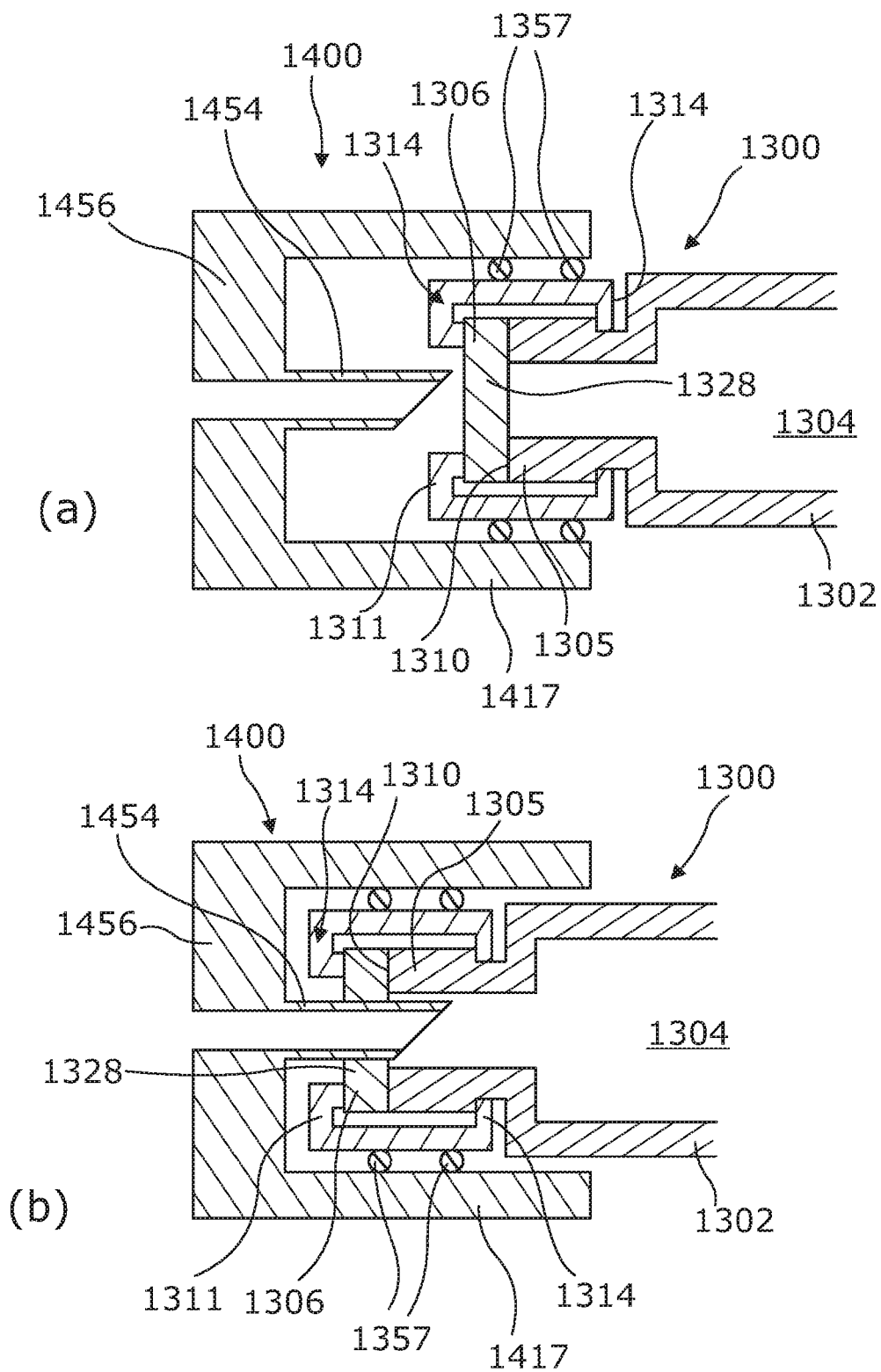

FIGS. 18(a) and 18(b) show an isometric view and an exploded view, respectively, of part of a variant of the medicament package of FIG. 17; and FIG. 19 shows schematic cross-sectional views of parts of another medicament package in use with a further dosing device, with the medicament package partially inserted (FIG. 19(a)) and fully inserted (FIG. 19(b)).

FIGS. 1 and 2 show a medicament package according to the invention in the form of a cartridge 100. The cartridge 100 comprises a straight-sided tubular body 102, which defines a cavity 104 for containing a medicament. The cavity 104 is closed at a first, distal end by a closure member in the form of an elastomeric bung 106, and a piston member or stopper 108 is received in the cavity 104 to prevent leakage of medicament through the second, the proximal end of the body 102. The medicament is therefore contained in the cavity 104 between the bung 106 and the stopper 108.

The bung 106 is partially received in the cavity 104, so that a ribbed outer surface 110 of the bung 106 forms a seal against the inner wall 112 of the body 102. A retaining lip 113 is formed on the inner wall 112 of the body 102 at the distal end of the body 102, so that the bung 106 is retained in the body 102 both by the lip 113 and by the frictional fit between the bung 106 and the inner wall 112.

A generally tubular coupling element 114 is fitted to the distal end of the body 102. The coupling element 114 is formed from a rigid polymer, for example polyoxymethylene (POM) or polypropylene (PP), and includes a flange 116, which abuts the distal end of the body 102. As shown most clearly in FIG. 2, a skirt 118 extends proximally from the flange 114. The bung 106, which is formed from an elastomer (which may, for example, by a halobutyl), is overmoulded onto the skirt 118 so that the coupling element 114 is retained by the bung 106.

A tubular sleeve or nose 122 extends distally from the flange 116 of the coupling element 114. An annular projection 124 is formed around the nose 122. The annular projection comprises a ramp formation having a ramped distal face 125 (i.e. a face disposed at an inclined angle with respect to the long axis of the cartridge 100), and a proximal face 127 which is generally perpendicular to the long axis of the cartridge 100. An annular lip 132 is disposed around the distal end of the nose 122.

A portion of the bung 106 extends distally into the nose 122 of the coupling element 114. A bore 126 extends inwardly from the distal end of the bung 106 and is closed at its proximal end by a part of the bung formed as a thin membrane or septum 128.

It will be appreciated that the bung 106 serves both to attach the coupling element 114 to the body 102 and to seal the cavity 104 by means of the lateral seal between the bung 106 and the inner wall 112 of the body 102 and the septum 128.

The body 102 is preferably made from glass, although other materials (including biocompatible and pharmacologically inert plastics materials) could be used.

The stopper 108 is slidable within the body 102 and includes a recess 130 to receive a plunger (not shown) for driving the stopper 108 in a distal direction to eject medicament from the cartridge 100 in use. However, in other embodiments, the stopper may be formed without a recess, or may include an alternative arrangement for engagement with a plunger.

As will now be described, the projection 124 on the nose 122 of the coupling element 114 defines an engagement formation that is arranged to cooperate with a corresponding engagement part of a dosing device and serve to clip the cartridge 100 to the dosing device. By providing different types of dosing device with the appropriate engagement part, the cartridge 100 can be used with several different types of dosing device.

Figure 3:
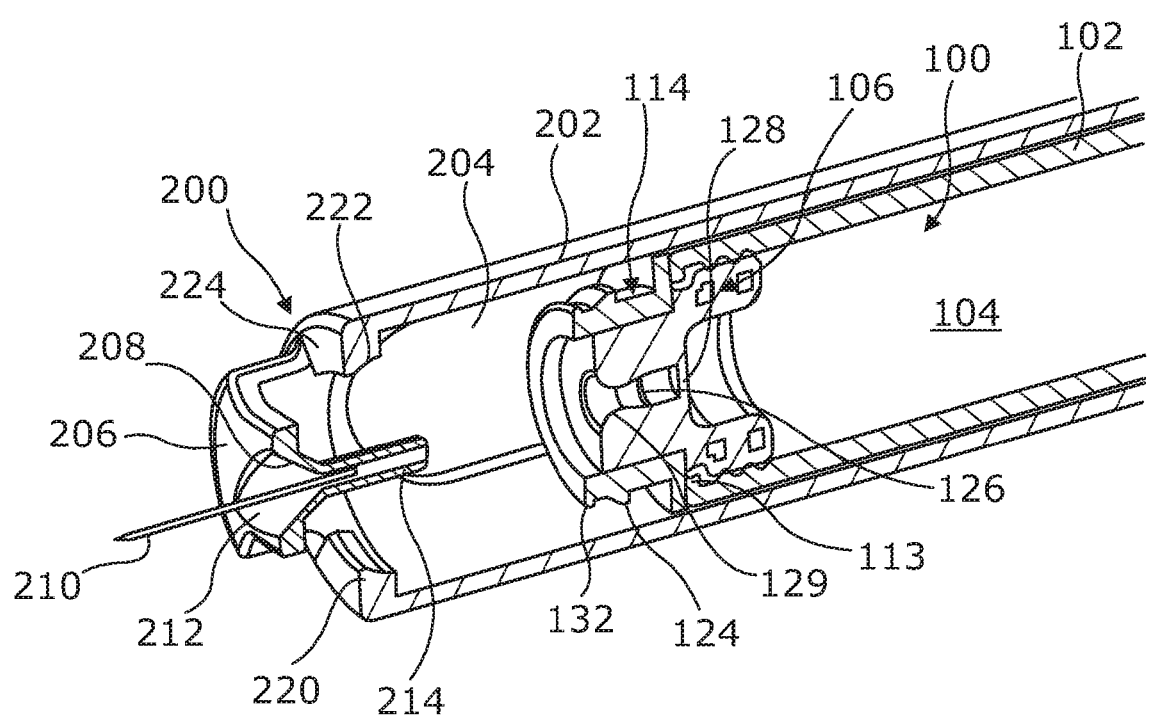
FIG. 3 is a cut-away isometric view of a syringe device with the medicament package of FIG. 1 partially inserted.
Figure 5:
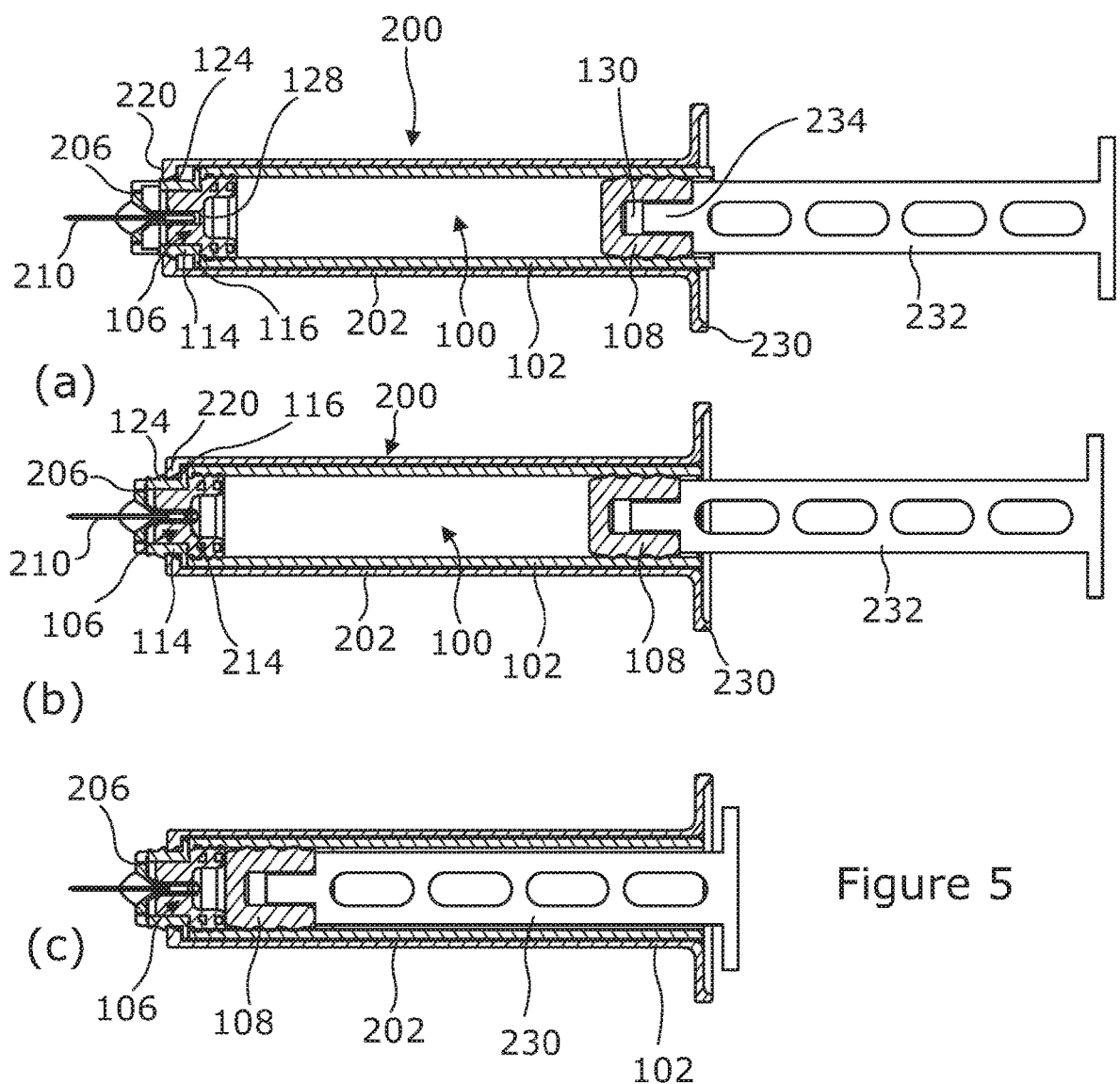
FIG. 5 shows cross-sectional views of the syringe device of FIG. 3 with the medicament package at a first insertion position (FIG. 5(a)), at a second insertion position (FIG. 5(b)), and after injection of the medicament (FIG. 5(c))

FIGS. 3 to 5 show one example of a dosing device that is designed for use with the cartridge 100. In this example, the dosing device is a disposable injection syringe intended for delivery of a single dose of medicament.

As shown in FIG. 3, the syringe 200 comprises a generally tubular body or housing 202 for receiving the cartridge 100. The housing 202 includes a viewing window 204 to allow the cartridge 100 to be seen by the user.

Referring additionally to FIG. 4(a), a reduced-diameter distal part of the housing 202 forms a needle holder 206 of the syringe 200. The needle holder 206 includes a recess 208 in its distal face in which a hypodermic needle 210 is retained with a polymeric seal 212. A sealing element release member in the form of a tubular piercing member 214 extends from a proximal face of the needle holder 206 to project into the interior of the housing 202.

The syringe 200 includes cartridge connector means to allow the cartridge 100 to be clipped to the syringe 200. Two clips 220 extend inwardly from the inside wall of the housing 202 adjacent the needle holder 206. Each clip 220 comprises a ramp formation having a ramped proximal face 222 and a distal face that is generally perpendicular to the long axis of the housing 202. The clips 220 act as engagement parts that are arranged to cooperate and engage with the coupling element 114 of the cartridge 100 as the cartridge 100 is inserted into the housing 202 and pushed in a distal direction, as will now be described.

FIG. 4(b) shows the cartridge 100 inserted in the housing 202 in a first insertion position. In this position, the lip 132 at the distal end of the coupling element 114 has been pushed past the clips 220. The ramped proximal faces 222 of the clips 220 bear against the correspondingly ramped distal face 125 of the projection 124 of the coupling element 114 to resist further movement of the cartridge 100 in the distal direction. In this first insertion position, the piercing member 214 is located in the bore 126 of the bung 106, but the septum 128 is not pierced. Accordingly, in this position, the medicament remains sealed within the cavity 104 of the cartridge 100, but the cartridge 100 is retained in the syringe device 200 by cooperation of the clips 220 and the lip 132.

The bore 126 provides a seal arrangement for the piercing member 214. In particular, the walls of the bore 126 are shaped so that the bung 106 forms an annular seal around the piercing member 214 when the piercing member 214 is received in the bore 126. In this way, the proximal tip of the piercing member 214 can be kept sterile in an enclosed chamber adjacent to the septum 128, with the chamber being closed at its distal end by the seal formed inside the bore 126. In the illustrated example, the walls of the bore 126 are shaped to define a narrowed region 129 of the bore 126 that is resilient to press against the piercing member 214 in order to form the annular seal. The narrowed region 129 of the bore 126 thus provides a sealing surface of the seal arrangement.

When a sufficient distal force is applied to the cartridge 100, the ramped faces 125, 222 of the projection 124 and the clips 220 cooperate to force the clips 220 radially outwards to allow the projection 124 to move past the clips 220.

FIG. 4(c) shows the situation once the cartridge 100 has been pushed fully home into the housing 202, to adopt a second insertion position. In this position, the proximal face 127 of the projection 124 bears against the distal face 224 of each clip 220 to block movement of the cartridge 100 in a proximal direction. Further movement of the cartridge 100 in the distal direction is also blocked because the clips 220 bear against the flange 116 of the coupling element 114. In this way, the cartridge 100 is clipped securely into the housing 202 of the syringe.

The position of the septum 128 with respect to the coupling element 114 is such that, when the cartridge 100 moves into the second insertion position, the septum 128 is pierced by the piercing member 214, allowing medicament to flow from the cavity 104 through the piercing member 214 and into the hypodermic needle 210. The annular seal formed between the walls of the bore 126 and the piercing member 214 at the narrowed region 129 of the bore 126 is maintained to preserve the sterility of the piercing member 214 and to guard against leakage of medicament.

FIG. 5 shows a possible sequence of steps in operation of the syringe 200. Referring firstly to FIG. 5(a), it can be seen that a proximal end of the syringe housing 202 is shaped to form two outwardly-extending finger tabs 230. The syringe 200 is fitted with a plunger 232 having an end piece 234 that is retained in the recess 130 in the stopper 108.

In FIG. 5(a) the cartridge 100 is in its first insertion position, in which the septum 128 remains intact. In this stage, the syringe 200 may be packaged and stored, with the medicament sealed within the cartridge 100. A removable needle shield (not shown) can be used to seal the distal end of the needle 210. With the needle shield in place, and with the seal formed between the piercing member 214 and the bore 126 of the bung 106, the whole of the medicament flow path from the piercing member 214 to the distal end of the needle 210 remains sterile until the device is prepared for use, even if the syringe 200 is not itself contained in sterile packaging.

To prepare the syringe 200 for use, the needle shield is removed and the cartridge 100 is moved distally with respect to the syringe housing 202, for example by applying distal pressure to the plunger. The cartridge 100 moves to its second insertion position, shown in FIG. 5(b), in which the clips 220 are located between the projection 124 and the flange 116 of the coupling element 114. The septum 128 is pierced by the piercing element 214 to allow the medicament to reach the needle 210 and the plunger 232 can be depressed a short way to expel air and to verify medicament flow.

Once the needle 210 has been inserted in the skin, the plunger 232 can be depressed using thumb pressure to drive the stopper 108 in a distal direction towards the needle 210 to inject the medicament. The finger tabs 230 help the user to grip the syringe 200 during injection.

When the stopper 108 reaches the bung 106, as shown in FIG. 5(c), no more medicament can be injected and the needle 210 is withdrawn from the skin. The syringe 200, complete with the cartridge 100, is then discarded. It will be appreciated from FIG. 5(c) that the housing 202 of the syringe 200 is long enough to completely shroud the cartridge 100, therefore impeding access to the cartridge 100 to guard against tampering or unintentional disassembly of the device.

Figure 6:
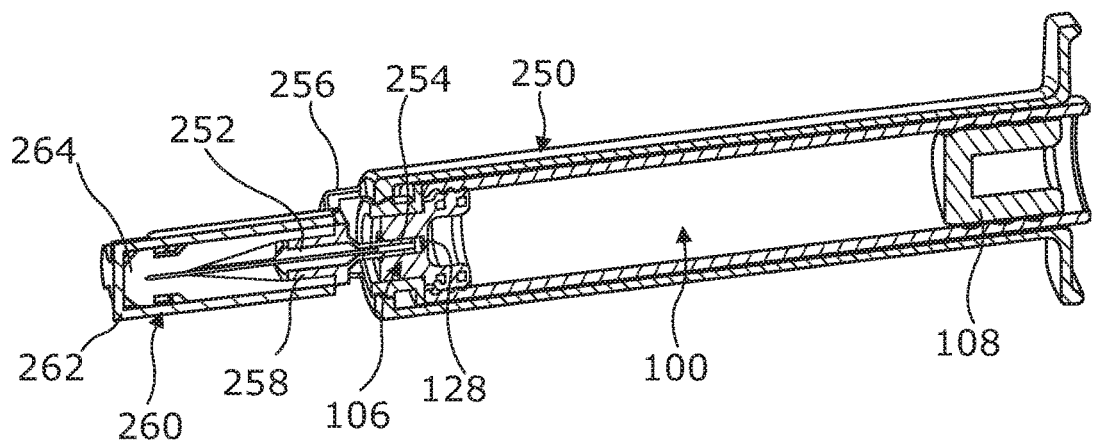
FIG. 6 is a cut-away isometric view of a variant of the syringe device of FIG. 3, with the medicament package at a first insertion position.

FIG. 6 shows a variant of the dosing device of FIGS. 4 and 5. In this variant, the dosing device comprises a syringe 250 that is similar to the syringe 200 of FIGS. 4 and 5, except in that the needle holder 256 includes a generally tubular distal extension 258. The needle 210 is retained in the tubular extension 258 by a polymeric seal 252.

A removable needle shield or cap 260 is fitted to the distal end of the syringe 250. The shield 260 comprises a generally tubular outer body 262 with a closed distal end and an open proximal end. An internal moulding 264 is retained in the outer body 262. A distal end of the internal moulding 264 is shaped to receive and protect the distal end of the needle 210 when the shield 260 is fitted to the syringe 250, and a proximal end of the internal moulding 264 is sized to receive the tubular extension 258 of the needle holder 256. The shield 260 is secured to the syringe 250 by a frictional fit between the internal moulding 264 and the tubular extension 258.

In the configuration illustrated in FIG. 6, the cartridge 100 is in its first insertion position with respect to the syringe 250. As described above with reference to FIGS. 4(b) and 5(a), in this position, the septum 128 of the cartridge bung 106 is not pierced by the piercing member 254 of the syringe 250. Accordingly, the medicament is still sealed within the cartridge 100.

Provided that the components of the syringe 250 are sterilised before assembly, sterility of the medicament-contacting and patient-contacting parts of the syringe 250 can be maintained when the syringe is in the configuration shown in FIG. 6. In particular, a seal is formed between the bung 106 and the piercing member 254 so that the sterility of the piercing member 254 is preserved, and the needle shield 260 fits tightly to the extension 258 to preserve sterility of the needle.

Accordingly, the syringe 250, together with the cartridge 100 fitted in the first insertion position, can conveniently be packaged in the state shown in FIG. 6 for sale, transport, storage and subsequent use in a clinical setting, optionally together with a plunger (not shown in FIG. 6) which may either be fitted to the stopper 108 or included separately in the package for subsequent assembly. As described above with reference to FIGS. 4(c), 5(b) and 5(c), to ready the syringe 250 for use, the cartridge 100 can be pushed into the second insertion position to pierce the septum 128 and then the stopper can be translated to deliver the medicament.

In the dosing devices shown in FIGS. 3 to 6, the septum 128 of the cartridge 100 is pierced by a dedicated piercing member 214 that is formed integrally with the needle holder 206 and that is distinct from the hypodermic needle 210. One advantage of this arrangement is that the diameter of the piercing member 214 and, correspondingly, the size of the bore 126 in the bung 106, can be larger than the diameter of the needle 210. However, it will be appreciated that different arrangements are possible. For example, the piercing member may comprise a separate component, such as a second needle, that is attached to the needle holder. In another example, the needle is double-ended and extends proximally from the needle holder, so that the proximal end of the needle forms the piercing member. In this case, manufacturing of the device may be simplified since it is not necessary to provide a separate piercing member.

The cartridge 100 of FIGS. 1 and 2 can also be used as replaceable cartridge in a reusable injection pen or pump device. In this example, this is achieved by fitting the cartridge 100 with an adaptor, as will be now described with reference to FIGS. 7 to 9.

Figure 7:
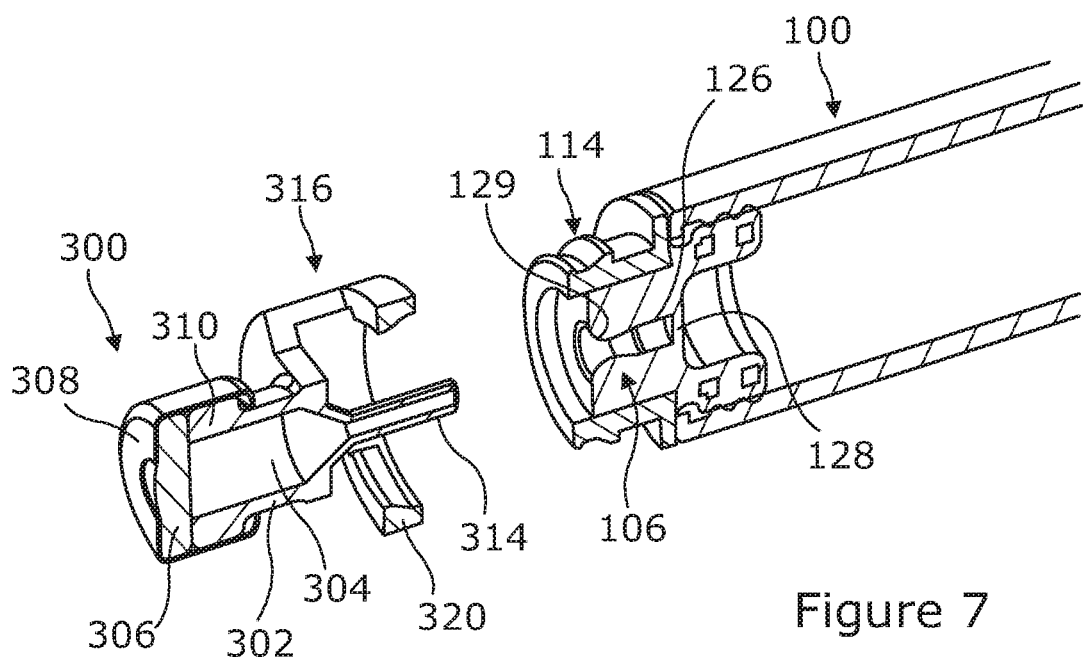
FIG. 7 is a cut-away isometric view of an adaptor device before attachment to the medicament package of FIG. 1.
Figure 8:
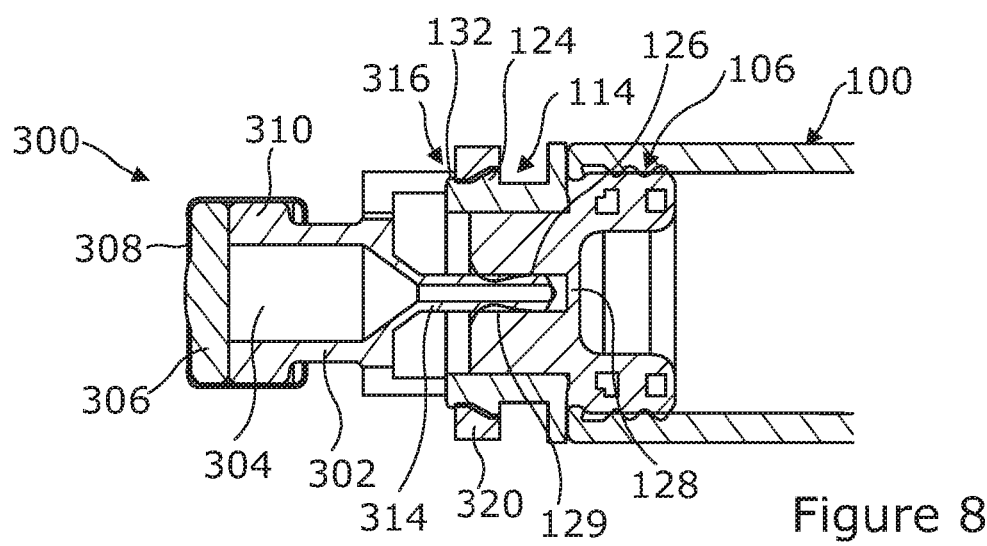
FIG. 8 is a cross-sectional view of the adaptor device of FIG. 7, with the medicament package in a first insertion position.

Referring to FIGS. 7 and 8, the adaptor 300 comprises an adaptor body 302. The adaptor body 302 is generally tubular to define a chamber 304 in the body 302. A distal end of the chamber 304 is sealed with a suitable adaptor seal, such as a self-sealing septum 306, which is secured to the distal end of the adaptor body 302 by a crimp closure or cap 308. The adaptor body 302 is formed with an outwardly projecting lip 310 to retain the crimp cap 308.

A tubular piercing member 314 extends proximally from the adaptor body 302, and the medicament chamber 304 is fluidly connected to bore of the piercing member 314.

The adaptor 300 also includes an engagement part 316 having two inwardly-extending clips 320 for engagement with the coupling element 114 of the cartridge. The clips 320 are similar in structure and function to the clips 220 of the syringe device 200 described above with reference to FIGS. 3 and 4, and the cartridge 100 can be clipped to the adaptor 300 in substantially the same way.

Accordingly, FIGS. 8 and 9(a) show the cartridge 100 in a first insertion position with respect to the adaptor 300, in which the clips 320 of the adaptor 300 are located between the lip 132 and the projection 124 of the coupling element 114, and in which the septum 128 of the cartridge bung 106 remains intact. The piercing member 314 is received in the bore 126 of the bung 106, and the walls of the bore 128 form an annular seal around the piercing member 314 at the narrowed region 129 of the bore 128 to preserve the sterility of the piercing member 314 and the chamber 304. Said another way, the proximal tip of the piercing member 314 is received in an enclosed chamber defined by the septum 128 and the annular seal. FIG. 9(b) shows the cartridge 100 in a second insertion position, in which the clips 320 of the adaptor 300 are located between the projection 124 and the flange 116 of the coupling element 114 to securely couple the adaptor 300 to the cartridge 100 and in which the septum 128 has been pierced by the piercing member 314.

Once the septum 128 has been pierced, medicament can flow from the cavity 104 in the cartridge 100, through the piercing member 314 and into the chamber 304 in the adaptor 300. The medicament is still sealed within the chamber 304 by the adaptor septum 306.

The combined cartridge and adaptor assembly 350 of FIG. 9(b) can then be used in place of a dedicated cartridge in an injection pen device, a pump device, or similar. Once the assembly 350 has been installed in the device, the adaptor septum 306 can be pierced by attachment of a disposable hypodermic needle or other piercing member.

To suit different devices, the adaptor 300 may be sized for compatibility with a particular medicament dosing device. For example, the adaptor body 302 may have an outer diameter that differs from the outer diameter of the coupling element 114 of the cartridge. Depending on the device for which it is intended, the adaptor 300 may also be provided with a suitable fitting (such as a screw thread or a luer lock) for attachment of a disposable needle, a delivery tube or other apparatus. Instead of a septum, the adaptor seal may comprise a valve or other suitable sealing means.

Figure 10:
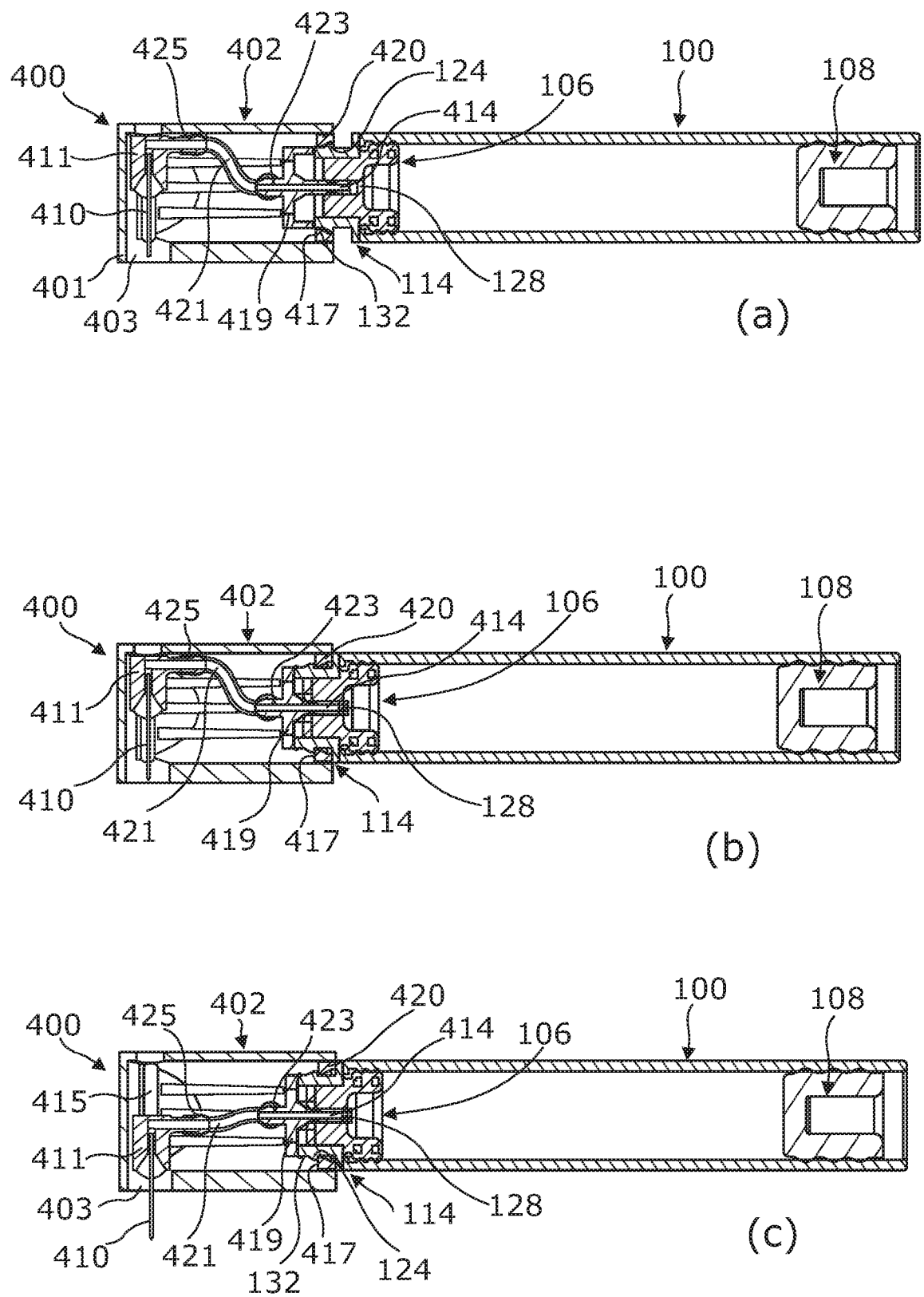
FIG. 10 shows cross-sectional views of a dosing device with a medicament package according to FIG. 1 in a first insertion position (FIG. 10(a)), in a second insertion position with the needle retracted (FIG. 10(b)) and in the second insertion position with the needle deployed (FIG. 10(c))
Figure 11:
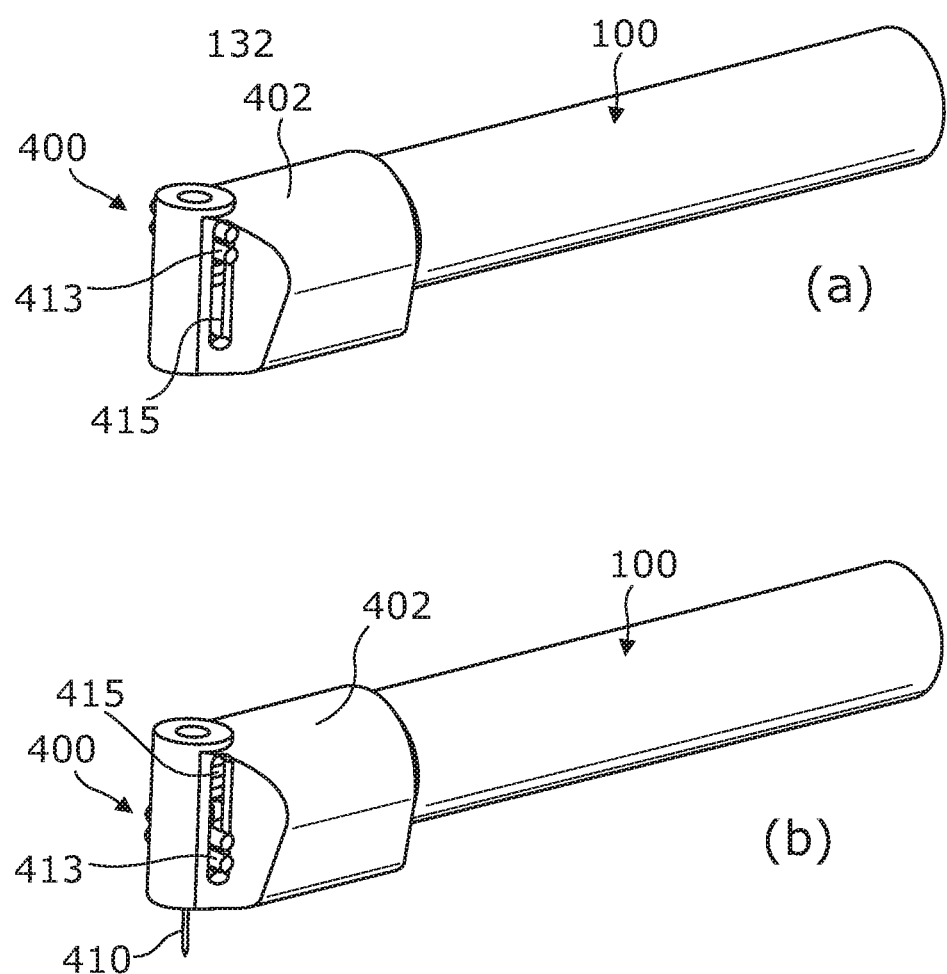
FIG. 11 shows isometric views of the dosing device and medicament package of FIG. 10 with the needle retracted (FIG. 11(a)) and with the needle deployed (FIG. 11(b))

FIGS. 10 and 11 show another example of a dosing device that is designed for use with the cartridge 100 of FIGS. 1 and 2. In this case, the dosing device is a 90-degree needle assembly 400 with a needle insertion mechanism that is suitable for use with, for example, a patch-style medicament pump.

The needle assembly 400 comprises a body 402 which houses a hypodermic needle 410 that is mounted to a moveable needle carriage 411. As best seen in FIGS. 11(a) and (b), the needle carriage 411 is guided for linear movement in the body 402 by way of pins 413 that extend through slots 415 formed in opposite walls of the body 402. The needle 410 is disposed perpendicularly to a base 401 of the body 402.

Referring back to FIG. 10, the needle assembly 400 also includes cartridge connector means to allow the cartridge 100 to be clipped to the needle assembly 400. The connector means comprises an aperture 417 formed in a proximal end of the body 402, and engagement parts clips 420 that are arranged at the periphery of the aperture 417. The clips 420 are formed integrally with the body 402.

The body 402 also houses a piercing member 414 in the form of a tube that projects proximally towards the aperture 417. In this example, the piercing member 414 is supported on a support frame 419 within the body 402, and the piercing member 414, the support frame 419 and the body 402 are formed together as a single component, for example by injection moulding.

The piercing member 414 is in fluid communication with the hypodermic needle 410 by means of a flexible tube 421. The flexible tube 421 is attached at a proximal end to a nipple 423 on the support frame 419. The bore of the nipple 423 is continuous with the bore of the piercing member 414. The tube 421 is attached at its distal end to a nipple 425 on the needle carriage 411, which is connected to the bore of the needle 410 by internal galleries in the needle carriage 411.

The clips 420 are similar in shape and function to the clips 220 of the syringe device 200 described above with reference to FIGS. 3 to 5. Accordingly, in the dosing device of FIGS. 10 and 11, when the cartridge 100 is inserted into the aperture 417 the cartridge 100 clips to the adaptor in one of two insertion positions with respect to the needle assembly 400. When clipped in place, the cartridge 100 extends parallel to the base 401 of the body.

FIG. 10(a) shows the cartridge 100 in a first insertion position, in which the clips 420 of the needle assembly 400 are located between the lip 132 and the projection 124 of the coupling element 114, and in which the septum 128 of the cartridge bung 106 remains intact. An annular seal is formed between the bung 106 and the piercing member 414 to preserve the sterility of the piercing member 414. FIG. 10(b) shows the cartridge 100 in a second insertion position, in which the clips 420 of the adaptor 400 are located between the projection 124 and the flange of the coupling element 114 to securely couple the needle assembly 400 to the cartridge 100. In this position, the septum 128 has been pierced by the piercing member 414, and medicament can flow from the cartridge 100 to the needle 410 by way of the piercing member 414 and the flexible tube 421.

In use, the needle carriage 411 is initially located in a retracted position, as shown in FIGS. 10(a) and 10(b) and in FIG. 11. In the retracted position, the needle 410 is concealed within the body 402. The base 401 of the body 402 can be adhesively or otherwise secured to the skin of a patient, and the needle carriage 411 can then be translated (either manually or by mechanical means) to extend the needle out of the body 402 through an aperture 403 in the base 401 to enter the patient's skin. Medicament can then be delivered through the needle 410 by translation of the stopper 108 of the cartridge 100. In this way, the needle assembly 400 and attached cartridge 100 can be used for example in a patch pump, in which the stopper 108 is driven by a plunger (not shown) of the pump.

It will be appreciated from the foregoing that the cartridge 100 described with reference to FIGS. 1 and 2 is suitable for use with multiple different types of dosing device, including disposable syringes, injection pens, auto injectors, pump devices and infusion sets. Because in each case the primary packaging for the medicament is the same, validation and approval of such a cartridge 100 allows the same medicament to be delivered in many different types of device without increased costs.

Several variations and modifications of the cartridge of FIGS. 1 and 2 are possible. For example, in one variation (not shown), the lip 113 at the distal end of the body 102 can be omitted and the bung 106 can be retained in the cavity 104 solely by the frictional fit between the bung 106 and the inner wall 112 of the body 102. In this variant, the body 102 can take the form of a simple straight-sided tube, resulting in lower component and manufacturing costs and in simpler manufacturing processes than would otherwise be the case.

In the illustrated example, the bung 106 is overmoulded onto the skirt 118 of the coupling element 114. However, the bung and the coupling element may be attached to one another in a different way, for example by an alternative mechanical attachment or by use of a suitable adhesive. In such cases, the collar 118 of the coupling element 114 may not be present.

Furthermore, in the embodiment illustrated in FIGS. 1 and 2, the stopper of the cartridge is slidable linearly towards the distal end of the body, but other arrangements are possible. For example, the stopper may rotate as it moves towards the distal end of the body. In one such variant (not shown), the stopper and the body may be formed with complementary screw threads, such that the stopper can be driven to rotate by the plunger, or by another suitable driving means, to cause movement of the plunger in the distal direction to eject medicament from the cartridge.

FIG. 12 shows a medicament cartridge 500 according to another embodiment of the invention. Referring particularly to FIG. 12(a), the cartridge 500 comprises a generally tubular body 502, which defines a cavity 504 for the medicament. As in the cartridge of FIGS. 1 and 2, in the cartridge 500 of FIG. 12 the cavity 504 is closed at a first, distal end by a closure member in the form of an elastomeric bung 506, and a piston member or stopper 508 is received in the cavity 504 to prevent leakage of medicament through the second, proximal end of the body 502. The medicament is therefore contained in the cavity 504 between the bung 506 and the stopper 508.

In this embodiment, the body 502 includes a reduced-diameter distal portion 503, forming a neck of the body 502. An annular lip or collar 505 is provided at the distal end of the neck 503 of the body 502. In the illustrated example, the neck 503 and the collar 505 are integrally formed with the body 502, although in other examples the neck 503 and/or the collar 505 may be discrete components.

The bung 506 comprises a flange portion 507 at its distal end and generally tubular insertion portion 509 that extends proximally from the flange portion 507. The insertion portion 509 is received in the neck 503, so that a ribbed outer surface 510 of the insertion portion 509 of the bung 506 forms a seal against the inner wall 512 of the body 502 at the neck 503.

A bore 526 extends through the tubular portion 509 of the bung 506, and the bore 526 is closed by a pierceable membrane or septum 528. The septum 528 is formed integrally with the bung 506.

Referring additionally to FIGS. 11(b), 11(c) and 12, a coupling element 514 is clipped to the distal end of the body 502. The coupling element 514 includes a cap portion 515 and a plurality of legs 517 that extend proximally from the cap portion 515 and that are separated from one another by slots 519.

As shown most clearly in FIG. 13, an annular channel 523 is formed in the inside face of the cap portion 515 to receive the collar 505 of the neck 503. The inside face 521 of each leg 517 is ramped so that, when the coupling element 514 is pushed over the distal end of the body 502 and the bung 506 during assembly, the legs 517 are urged outwardly to pass over the collar 505 of the neck 503 and to guide the collar 505 into the channel 523. In this way, the coupling element 514 is securely attached to the body 502 by engagement of the collar 505 with the channel 523 and the bung 506 is retained in the neck 503 by the coupling element 514.

The outer face of the coupling element 514 includes a first annular recess 542 disposed next to the distal end of the legs 517, and a second annular recess 544 spaced distally from the first annular recess 542 and next to the distal end of the coupling element 514. The cap portion 515 includes an aperture 546 to allow access to the septum 528 through the coupling element 514.

Figure 14:
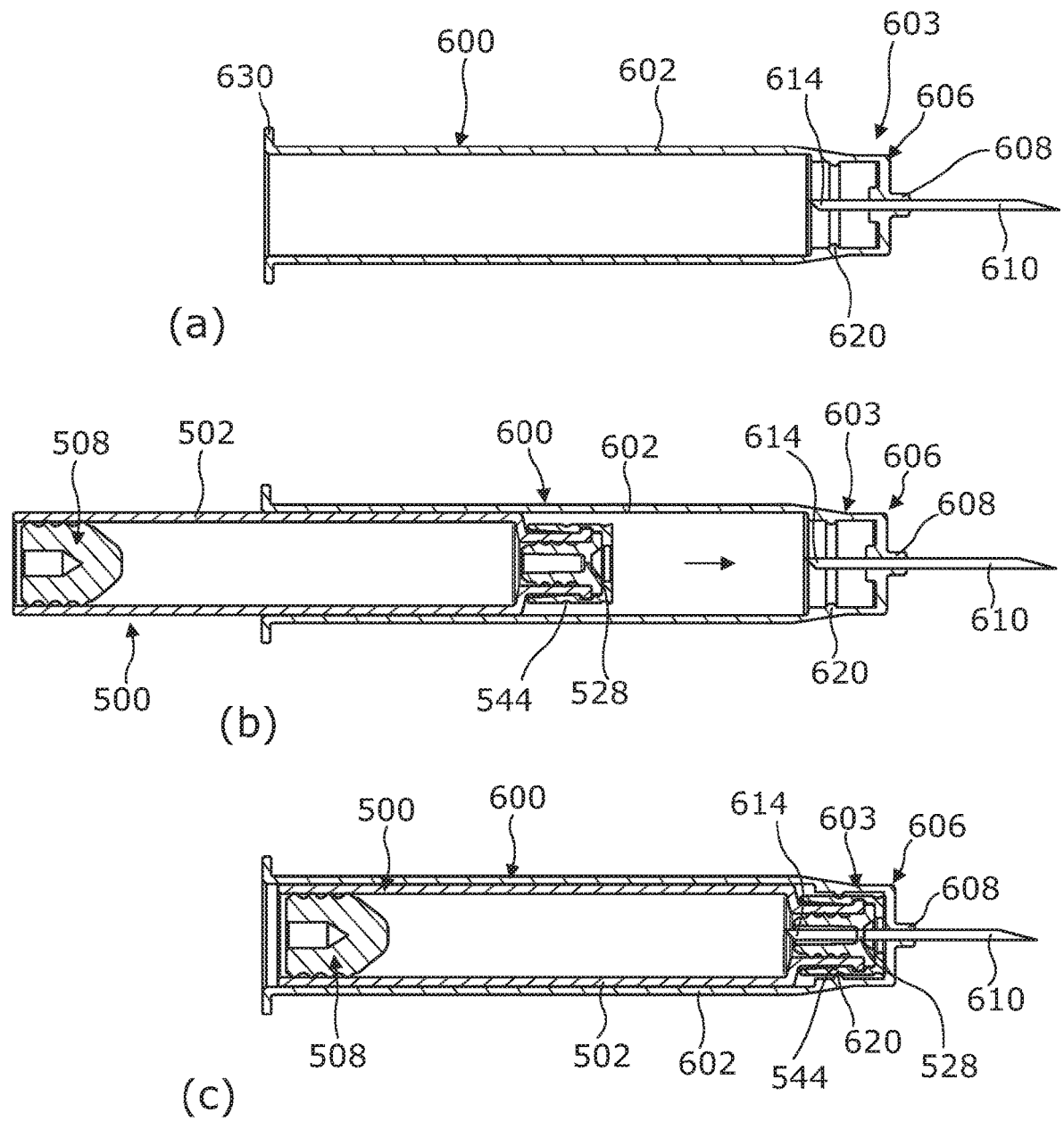
FIG. 14 shows cross-sectional views of another syringe device, without a medicament package (FIG. 14(a)), with the medicament package of FIG. 12 partially inserted (FIG. 14(b)), and with the medicament package of FIG. 12 fully inserted (FIG. 14(c))

One application of the cartridge 500 in a dosing device in the form of a disposable injection syringe intended for delivery of a single dose of medicament will be now be described with reference to FIG. 14.

Referring first to FIG. 14(a), the syringe device 600 comprises a generally tubular body or housing 602 for receiving the cartridge 500 (not shown in FIG. 14(a)). The housing 602 includes a reduced-diameter distal part 603 that terminates with a needle holder 606 that closes the end of the housing 602. The needle holder 606 includes a tubular sleeve 608 in its distal face in which a hypodermic needle 610 is retained. The housing 602 also includes finger tabs 630 at its proximal end.

A proximal end 614 of the needle 610 projects from the needle holder 606 into the interior of the housing 602. An annular projection or ridge 620 is formed on the inside wall of the housing 602 in the reduced diameter portion 603 to provide cartridge connector means.

The projection 620 is arranged to engage with the annual recesses 542, 544 of the coupling element 514 of the cartridge 500 as the cartridge 500 is inserted into the housing 602 and pushed in a distal direction, as will now be described.

FIG. 14(b) shows the cartridge 500 during insertion into the housing 602. As the distal end of the cartridge 500 approaches the needle holder 606, the proximal end 614 of the needle 610 pierces the septum 528.

Once the coupling element 514 of the cartridge 500 is pushed home into the reduced diameter portion 603 of the housing, as shown in FIG. 14(c), the annular projection 620 locates in the first annular recess 544 of the coupling element 514, so as to clip the cartridge 500 to the housing 602. With the cartridge 500 in this position, medicament can flow from the cartridge 500 through the needle 610 for injection.

It will be appreciated that a plunger (not shown in FIG. 14) can be attached to the stopper 508 to allow the stopper 508 to be moved distally to dispense the medicament through the needle 610. After injection of the medicament, the syringe 600, together with the cartridge 500, can be disposed of.

Figure 15:
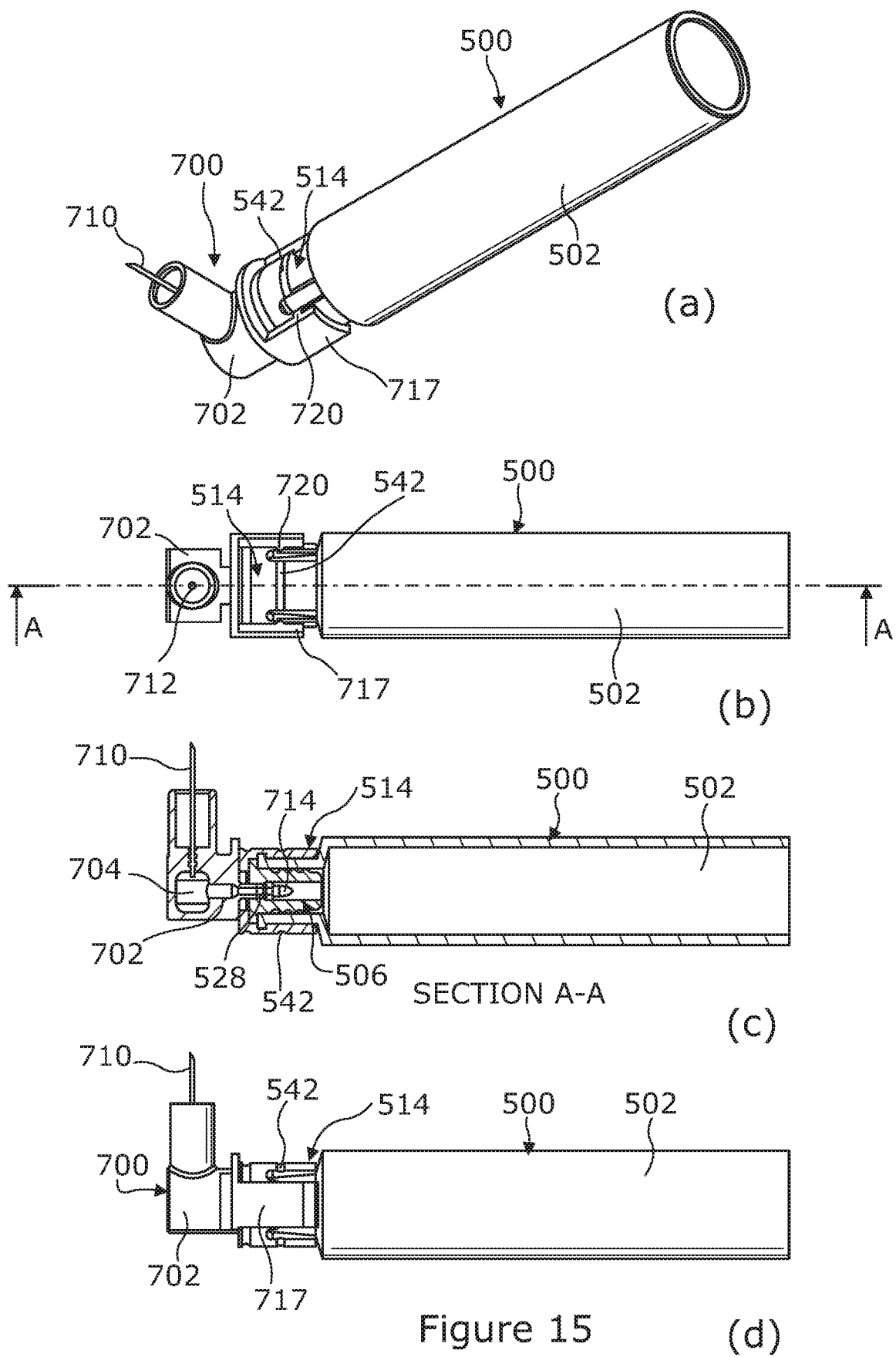
FIG. 15 shows another dosing device coupled to the medicament package of FIG. 12, in isometric, bottom, side sectional and side views.

FIG. 15 shows the cartridge 500 in use with another dosing device. In this case, the dosing device comprises a 90-degree needle assembly 700, for example for use with an infusion patch pump.

The needle assembly 700 comprises a body 702 and a hypodermic needle 710 that is moulded into the body 702. As can be seen in FIG. 15(c), the needle 710 is in fluid communication with an internal chamber 704 of the body 702. A tubular piercing member 714, also in fluid communication with the chamber 704, extends from the body 702 at a 90-degree angle to the axis of the needle 710.

The needle assembly 700 also includes cartridge connector means comprising two arms 717 that extend from the body 702 either side of and generally parallel to the piercing member 714. As shown in FIGS. 15(a) and 15(b), the inside surface of each arm 717 is provided with a ridge or projection 720 for engagement with the corresponding first annular recess 542.

As shown in FIG. 15, the needle assembly 700 can be clipped to the cartridge 500 by inserting the coupling element 514 of the cartridge 500 into the space between the arms 717. When in place, the arms 717 are positioned to embrace the coupling element 514 therebetween, and the projections 720 on the arms 717 locate in the first annular recess 542 to secure the needle assembly 700 and the cartridge 500 together.

During insertion of the cartridge 500, the piercing member 714 of the needle assembly 700 pierces the septum 528 of the bung 506 of the cartridge 500. This allows medicament to flow from the cartridge 500 to the needle 710, by way of the internal chamber 704 in the needle assembly 700. The needle assembly 700 and attached cartridge 500 can be used for example in a patch pump, in which the stopper (not shown) of the cartridge 500 is driven by a plunger (not shown) of the pump.

Although not illustrated in the figures, it will be appreciated that the second annular recess 544 in the coupling element 514 of the cartridge 500 could serve to provide an intermediate attachment position for the cartridge 500 with respect to a device in which the cartridge 500 is engaged with the device but in which the septum 528 remains intact, as described above with reference to the cartridge 100 of FIGS. 1 and 2. When applied to the FIG. 14 device, a seal may be formed between the annular recess 544 of the coupling element and the annular projection 620 of the housing. In other variants, the septum 528 could be spaced proximally from the end of the bung 506 by a bore or passage that is sized to form a seal around the piercing member or needle when the piercing member or needle is received in the bore or passage.

As illustrated by the above examples, the cartridge 500 shown in FIG. 11 is also suitable for use with multiple different types of dosing device, including disposable syringes, injection pens, auto injectors, pump devices and infusion sets. It will also be appreciated that, in some applications, the cartridge 500 of FIG. 11 could also be used without the coupling element 514.

Figure 16:
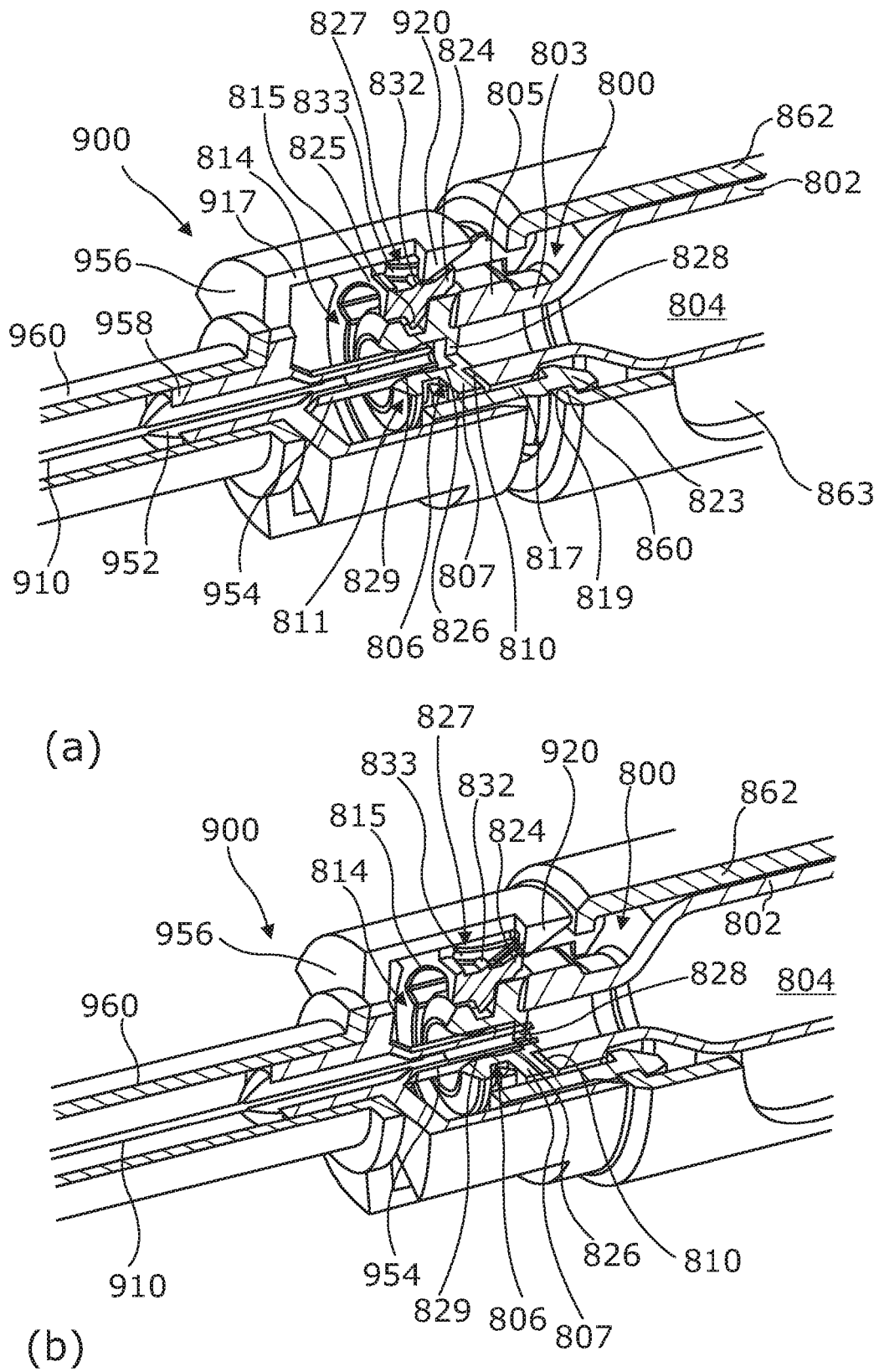
FIG. 16 shows cut-away isometric views of a further medicament package in use with another dosing device, with the medicament package partially inserted (FIG. 16(a)) and fully inserted (FIG. 16(b))

FIGS. 16(a) and 16(b) show a medicament cartridge 800 according to a further embodiment of the invention, in use with a dosing device 900. Only part of the cartridge 800 and the dosing device 900 are shown in FIG. 16. As in the cartridges described above with reference to FIGS. 1 and 2 and FIG. 12, the cartridge 800 of FIGS. 16(a) and 16(b) comprises a generally tubular body 802, which defines a cavity 804 for the medicament. Referring to FIG. 16(a), the cartridge 800 is closed at a first, distal end by a closure member 806. A piston member or stopper (not shown in FIG. 16) is received in the cavity 804 to close the second, proximal end of the body 802 and to retain the medicament in the cavity 804 between the closure member 806 and the stopper.

The container body 802 includes a reduced-diameter distal portion 803, forming a neck of the container body 802. An annular lip or collar 805 is provided at the distal end of the neck 803 of the container body 802. The closure member 806 comprises a sealing disc 807 having a flat proximal face 810 that forms a seal against the distal end of the collar 805. A mushroom-shaped throat 811 of the closure member 806 extends distally from the sealing disc 807. The throat 811 includes a bore 826 that extends from the distal end of the closure member 806, and a proximal end of the bore 826 is closed by a septum 828. The distal end of the throat 811 is flared outwardly. The walls of the bore 826 are shaped to define a narrowed region 829 of the bore 826.

A coupling element 814 is clipped to the distal end of the container body 802 to keep the closure member 806 in position. The coupling element 814 comprises an annular body or ring 815 and a plurality of legs 817 that extend proximally from the ring 815. In the illustrated example, three legs 817 are present, with two of the legs 817 visible in FIG. 16.

The proximal end of each leg 817 is shaped to define a clip formation 823 on the inside of each leg 817. The clip formation 823 has a ramped proximal face to allow the coupling element 814 to be pushed over the collar 805 of the container body 802, and a distal face of the clip formation 823 is oriented normally to the container axis to bear against the proximal side of the collar 805. The legs 817 are held in place by a clamping band 860, which in this example is disposed at the distal end of a container sleeve 862 in which the container body 802 is received. The clamping band 860 locates in a circumferential recess 819 formed on the outside face of each leg 817.

A plurality of circumferentially-extending tabs 825 are disposed on the inside of the ring 815 of the coupling element 814. The tabs 825 locate between the flared end of the throat 826 and the sealing disc 807 of the closure member 806 to retain the closure member 806. With the clip formations 823 of the legs 817 in position on the proximal side of the collar 805 and held in place by the clamping band 860, the tabs 825 act to apply a clamping force to the closure member 806 that keeps the sealing disc 807 of the closure member 806 in sealing contact with the distal end of the collar 805.

The outer wall of the ring 815 of the coupling element 814 includes three angularly-spaced recesses 827, disposed between each adjacent pair of legs 817. The recesses 827 are arranged for cooperation with corresponding clips 920 of the dosing device 900. The inner face of each recess 827 is shaped to define a ramp formation 824 at the proximal end of the coupling element 814 and a pair of ridge formations 832 disposed at axially spaced locations between the ramp formation 824 and the distal end of the coupling element 814. The side walls 833 of the recesses 827 are shaped so that the recesses 827 are widened in the circumferential direction towards the distal end of the coupling element 814, to help guide the clips 920 of the dosing device 900 into the recesses 827 when the cartridge 800 is inserted into the dosing device 900.

In this example, the dosing device 900 is in the form of an attachable needle assembly, and includes a needle holder 956 that is similar to the needle holder 256 described above with reference to FIG. 6. Thus, in the dosing device 900 of FIG. 16, the needle holder 956 includes a generally tubular distal extension or sleeve 958. A hypodermic needle 910 is retained in the sleeve 958 by a polymeric seal 952. The distal end (not shown) of the needle 910 is protected by a needle cap 960, only part of which is visible in FIG. 16. In this case, the needle cap 960 is of a single-piece design and comprises a rigid tube having a closed distal end (not shown) and a proximal end that is a frictional fit around the tubular extension 958 of the needle holder 956. The needle 910 is in fluid communication with a tubular piercing member 954 that extends proximally from the needle holder 956. Three arms 917 extend proximally from the periphery of the needle holder 956, and the aforementioned clips 920 are disposed at the proximal ends of the arms 917. The arms 917 and the clips 920 provide a cartridge connector of the needle assembly.

In the configuration illustrated in FIG. 16(a), the cartridge 800 is in a first insertion position with respect to the needle assembly 900. In this first insertion position, each clip 920 of the needle assembly 900 is located in a recess 827 of the coupling element 814, on the distal side of the corresponding ramp formation 824. Distal movement of the cartridge 800 with respect to the needle assembly 900 beyond the first insertion position is resisted by abutment of the clips 920 with the ramp formations 824. The ridge formations 832 serve to guard against proximal movement of the cartridge 800 with respect to the needle assembly 900.

When in this first insertion position, the piercing member 954 of the needle assembly 900 is received in the bore 826 of the closure member. However, the septum 828 of the closure member 806 is not pierced by the piercing member 954 and the medicament remains sealed in the cavity 804. Furthermore, a seal is formed between the narrowed region 829 of the bore 826 of the closure member 806 and the outer surface of the piercing member 954, to enclose the proximal end of the piercing member 954 in a chamber adjacent to the septum 828. In this way, the sterility of the proximal end of the piercing member 954 can be preserved, and hence the flow path through the piercing member 954 and the needle 910, along with the distal end of the needle 910, remains sterile.

FIG. 16(*b*) shows the situation where the cartridge 800 has been moved distally with respect to the needle assembly 900 into a second insertion position, forcing the clips 920 of the needle assembly 900 over the ramp formations 824 of the coupling element 814. In this second insertion position, each clip 920 of the needle assembly 900 is located on the proximal side of the corresponding ramp formation 824 of the coupling element 814. Abutment between the distal sides of the clips 920 and the proximal sides of the ramp formations 824 prevents withdrawal of the cartridge 800 from the needle assembly 900. As a result of the distal displacement of the cartridge 800, the piercing member 954 has pierced the septum 828. Accordingly, with the cartridge 800 in the second insertion position, medicament can be dispensed from the needle 910 after removal of the needle cap 960, for example by the application of a suitable plunger (not shown) to drive the stopper (not shown) of the cartridge 800.

In the illustrated example, the container sleeve 862 associated with the clamping band 860 provides a housing that can be gripped by the user when the cartridge 800 is used in a manual syringe application. To this end, the container sleeve 862 includes an aperture or window 863 (see FIG. 16(*b*)) to allow inspection of the container body 802 and the medicament. In this application, the needle assembly 900 can be pre-fitted to the cartridge 800 in sterile conditions and the combination can be supplied to the user with the cartridge 800 in the first insertion position. When required for use, the cartridge 800 can be moved to the second insertion position to allow medicament flow through the needle 910.

The cartridge 800 and/or the needle assembly 900 could however be used in other applications such as auto-injectors, pen-type injectors, infusion pumps and so on, as previously described. In such applications, the container sleeve 862 may be used to increase the effective diameter of the cartridge 800 to allow the cartridge 800 to fit correctly in the cartridge holder of a device.

To assemble the cartridge 800 of FIG. 16, the closure member 806 can be placed onto the distal end of the body 802, so that the proximal face 810 of the closure member 806 contacts the distal end face of the collar 805. The coupling element 814 can then be pressed on to the distal end of the body 802 to engage the clip formations 823 behind the collar 805 and to clamp the closure member 806 in place. This operation can be performed after the cavity 804 has been filled with medicament, thus minimising the amount of trapped air within the cavity 804. It is also possible for the closure member 806 to be pre-fitted to the coupling element 814 and for the resulting assembly to be pressed on to the distal end of the body 802 is a single operation. In a variant of the cartridge 800 of FIG. 16, the closure member 806 is overmoulded on to or otherwise attached to a suitable formation of the coupling element 814.

FIGS. 17(*a*) and 17(*b*) show a medicament cartridge 1000 according to a further embodiment of the invention, in use with another dosing device in the form of a needle assembly 1100. The medicament cartridge 1000 and needle assembly 1100 of FIGS. 17(*a*) and 17(*b*) are similar to those described above with reference to FIGS. 16(*a*) and 16(*b*), and only the differences will be described in detail.

In this case, the cavity 1004 of the medicament cartridge 1000 is closed at its distal end by a closure member 1006 in the form of an elastomeric disc. The proximal face 1010 of the closure member 1006 forms a seal against the distal end of the collar 1005 of the container body 1002. The central region of the closure member 1006 provides a pierceable septum 1028.

As in the embodiment shown in FIGS. 16(*a*) and 16(*b*), in the FIGS. 17(*a*) and 17(*b*) embodiment the closure member 1006 is held in place by a coupling element 1014 that clips to the distal end of the container body 1002, with clip formations 1023 being provided to engage with the proximal side of the collar 1005 of the container body 1002. The clip formations 1023 are disposed at the proximal ends of a plurality of legs 1017 that extend proximally from a ring 1015 of the coupling element 1014.

In this case, the ring 1015 supports a tubular throat 1011 of the coupling element 1014. The throat 1011 is integrally formed with the coupling element 1014, and defines a generally frustoconical bore 1026. With the coupling element 1014 clipped in place on the distal end of the body 1002, the proximal end of the throat 1011 presses against the closure member 1006 to seal the closure member 1006 against the distal end of the collar 1005. The circumference of the throat 1011 is uninterrupted so that a sealing force is applied to the closure member 1006 around a complete circle.

The bore 1026 of the throat 1011 is arranged to receive the piercing member of the needle assembly 1100. In this embodiment, the piercing member includes an enlarged-diameter tubular boss 1155 and a reduced-diameter tip part 1154, with the boss 1155 disposed between the tip part 1154 and the needle holder 1156. An O-ring 1157 is mounted in an annular groove 1159 that is disposed adjacent to the proximal end of the boss 1155.

The needle assembly 1100 is otherwise similar to the needle assembly 900 described above with reference to FIGS. 16(*a*) and 16(*b*), and thus is provided with clips 1120 arranged to cooperate with ramp formations 1024 and ridge formations 1032 in respective recesses of the coupling element 1014.

FIG. 17(*a*) shows the cartridge 1000 in a first insertion position with respect to the needle assembly 1100, in which each clip 1120 is located on the distal side of the corresponding ramp formation 1024. In this position, the tip part 1154 of the piercing member of the needle assembly 1100 does not pierce the septum 1028 of the closure member 1006. The O-ring 1157 on the boss 1155 locates in an annular groove 1029 provided adjacent to the distal end of the bore 1026 of the throat 1011. In this way, the O-ring 1157 is positioned between the throat 1011 and the boss 1155 to form a seal that encloses the proximal end of the piercing member 1154 in a sterile chamber adjacent to the septum 1028.

In this case, the cartridge 1000 is held in the first insertion position by location of the O-ring 1157 in the groove 1029 of the boss 1155, such that the groove 1029 of the boss 1155 acts as a further engagement formation of the coupling element 1014, and the O-ring 1157 and corresponding groove 1169 act as a corresponding further engagement part of the needle assembly 1100.

To move the cartridge 1000 out of the first insertion position into the second insertion position, sufficient force must be applied to the cartridge 1000 in the distal direction to deform the O-ring 1157 enough to move the O-ring 1157 out of the groove 1029.

FIG. 17(b) shows the cartridge 1000 in the second insertion position with respect to the needle assembly 1100, with each clip 1120 of the needle assembly 1100 located on the proximal side of the corresponding ramp formation 1024 of the coupling element 1014. In this second insertion position, the piercing member 1154 has pierced the septum 1028 to allow medicament delivery through the needle 1110 after removal of the needle cap 1160. By virtue of the frustoconical shape of the bore 1026 of the throat 1011, when in the second insertion position the O-ring 1157 is spaced from the wall of the bore 1026.

To assemble the cartridge 1000 of FIGS. 17(a) and 17(b), the closure member 1006 can be placed onto the distal end of the body 1002 after medicament filling, and the coupling element 1014 can then be pressed on to the distal end of the body 1002 to clamp the closure member 1006 in place. Advantageously, in this embodiment, the closure member 1006 is of a standard form that is used to provide a septum in known cartridge-type medicament packages.

As in the embodiment of FIGS. 16(a) and 16(b), in the embodiment of FIGS. 17(a) and 17(b) the coupling element 1014 is held in place by a clamping band 1060 disposed at the distal end of a container sleeve 1062 in which the container body 1002 is received.

FIGS. 18(a) and 18(b) show a variant of the container of FIGS. 17(a) and 17(b), with part of the assembled container 1200 shown in FIG. 18(a) and an exploded view shown in FIG. 18(b). The variant of FIGS. 18(a) and 18(b) is identical to the container 1000 of FIGS. 17(a) and 17(b), and like reference numerals are used for like features.

In the variant of FIGS. 18(a) and 18(b), a container sleeve is not provided, and instead a clamping band 1260 in the form of a simple ring is provided. The outer diameter of the clamping band 1260 is approximately equal to the outer diameter of the container body 1002, so that the clamping band 1260 does not substantially increase the diameter of the container 1200.

FIGS. 19(a) and 19(b) show another variant of a medicament cartridge 1300, in use with another dosing device 1400. Only a distal part of the medicament cartridge 1300 and a proximal part of the dosing device 1400 are shown.

As in the examples of FIGS. 17 and 18, in the FIG. 19 arrangement the cavity 1304 of the cartridge 1300 is closed at its distal end by a closure member 1306 in the form of an elastomeric disc. The proximal face 1310 of the closure member 1306 forms a seal against the distal end of the collar 1305 of the container body 1302. The central region of the closure member 1306 provides a pierceable septum 1328.

The closure member 1306 is held in place by a generally tubular coupling element 1314 that is attached to the distal end of the cartridge body 1302. An inwardly-directed proximal flange 1023 of the coupling element 1314 engages with the proximal side of the collar 1305. An inwardly-directed distal flange 1311 of the coupling element 1314 presses against the closure member 1306 to seal the closure member 1306 against the distal end of the collar 1305.

A seal arrangement, in the form of one or more sealing rings 1357, is disposed on the cylindrical outer wall of the coupling element 1314. In the illustrated example, two such sealing rings 1357 are provided, although fewer or more sealing rings could be present. The sealing rings 1357 are preferably elastomeric O-rings, and are retained in position in respective annular grooves formed in the outer wall of the coupling element 1313.

The dosing device 1400 comprises a cartridge connector portion that includes a tubular socket 1417 that is open at its proximal end to receive the distal end of the cartridge 1300. The sealing rings 1357 of the coupling element 1314 are arranged to form a seal against the inner wall of the socket 1417. The piercing member 1454 extends proximally from a disc part 1456 of the dosing device 1400. Although not shown in FIG. 19, the bore of the piercing member 1454 is in fluid communication with a needle or cannula, as described with reference to the previous examples, and the needle or cannula is suitably sealed before use.

FIG. 19(a) shows the cartridge 1300 in a first insertion position with respect to the dosing device 1400. With the sealing rings 1357 in contact with the inner wall of the socket 1417, the proximal end of the piercing member 1454 is sealed in a sterile chamber adjacent to the septum 1328. When the cartridge 1300 is moved distally with respect to the dosing device 1400 into a second insertion position, shown in FIG. 19(b), the piercing member 1454 pierces the septum 1328 to allow medicament delivery.

Although not shown in FIG. 19, it will be appreciated that the coupling element 1314 of the cartridge 1300 could be arranged to engage with suitable engagement formations of the dosing device 1400 to allow the cartridge 1300 to be clipped or otherwise coupled to the dosing device 1400 upon insertion of the cartridge 1300 to the socket 1417. For example, the socket 1417 could be provided with suitably spaced annular recesses or grooves to locate with the respective sealing rings 1357 to locate the cartridge in the first and/or second insertion positions, or the coupling element 1314 could be provided with other engagement formations as described with reference to the previous examples. Alternatively, the friction that arises between the sealing rings 1357 and the socket 1417 may be sufficient to maintain the cartridge 1300 in its respective positions with respect to the dosing device 1400.

In a variant of the FIG. 19 example, the sealing rings could be retained in the socket of the dosing device, instead of on the coupling element. In this case, the coupling element may include one or more annular grooves or recesses or other suitable formations to locate on the sealing ring when the cartridge is coupled to the dosing device. In further variants, the sealing rings are replaced or supplemented by other seal forming means, such as annular ridges or projections on the coupling element and/or the socket that are dimensioned to form a sealing fit when the cartridge is coupled to the dosing device.

In all of the above examples, where a cartridge is described in use with a dosing device, it will be appreciated that the dosing device could be substituted with an adaptor, and vice versa.

The cartridge-type medicament packages described above with reference to FIGS. 1, 12, 16, 17, 18 and 19 employ a pierceable septum as a sealing element to seal the medicament in the cartridge. To release the medicament from the cartridge, the dosing device or adaptor includes a sealing element release member in the form of a piercing member that pierces the septum when the cartridge is inserted. It will however be understood that different arrangements for sealing the medicament in the package and for releasing the medicament are possible.

For example, whilst in the examples of FIGS. 1 and 12 the septum is formed integrally with a bung, in variations of these examples the septum may be a separate component that is supported or retained by a bung or by a support part of a closure member of a different form. As an alternative to a pierceable septum, the sealing element may be a valve component. For instance, the valve component may comprise one or more valve members that are biased to seal the cartridge and that can be moved to release the medicament by cooperation with a suitable valve opening member of the device or adaptor upon insertion of the cartridge. The valve opening member may, for example, comprise the proximal end of the needle or a dedicated tubular component similar to the piercing member of the devices shown in FIGS. 3 to 11, 16, 17, 18 and 19.

In another embodiment, the sealing element may be designed to open in response to an increase in pressure of the medicament when the stopper is moved towards the distal end of the cartridge to start medicament delivery, in which case a valve opening member or sealing element release member is not required. For example, a self-opening sealing element or valve component of this type may comprise an elastomeric septum divided by one or more slits into flexible valve members. In this case, the valve members seal against one another until the medicament pressure increases to cause the valve members to splay apart, releasing the seal. In another example, the septum is designed to rupture in response to an increase in pressure. In such cases, a seal arrangement that forms a seal between the coupling element and the dosing device may still be provided to maintain the sterility of the distal side of the sealing element and the flow path through the dosing device or adaptor.

It will be appreciated that further modifications and variations of the above-described examples are also possible without departing from the scope of the present invention as defined by the appended claims.

The invention claimed is:

1. A cartridge for packaging a medicament, the cartridge being suitable for use with multiple different types of dosing devices and comprising:
   a generally tubular body having an interior cavity;
   a closure member disposed at a distal end of the body and comprising a sealing element;
   a piston member disposed in the cavity to contain the medicament between the piston member and the sealing element;
   a coupling element disposed at the distal end of the body for coupling the cartridge to a dosing device or to an adaptor for a dosing device; and
   a seal arrangement comprising a passage for receiving a sealing element release member of the dosing device or adaptor,
      the passage comprising a sealing surface arranged to form a seal around the release member;
   wherein the coupling element is arranged for engagement with an engagement part of the dosing device or adaptor to clip the cartridge to the dosing device or adaptor upon insertion of the cartridge to the dosing device or adaptor;
   and wherein the seal arrangement is disposed distally with respect to the sealing element and is arranged to form a seal around the release member when the cartridge is coupled to the dosing device or adaptor.

2. A cartridge according to claim 1, wherein the coupling element is arranged to define first and second insertion positions for the cartridge with respect to the dosing device or adaptor.

3. A cartridge according to claim 2, wherein the sealing element is positioned such that, when the cartridge is in the first insertion position, the sealing element prevents release of the medicament from the cartridge and when the cartridge is in the second insertion position, the sealing element cooperates with the release member of the dosing device or adaptor to allow flow of the medicament from the cartridge.

4. A cartridge according to claim 3, wherein the coupling element comprises first and second engagement formations for cooperation with the dosing device or the adaptor thereby to define the first and second insertion positions.

5. A cartridge according to claim 2, wherein the seal arrangement is arranged to form a seal around the release member when the cartridge is in the first insertion position.

6. A cartridge according to claim 2, wherein the coupling element comprises an engagement formation for cooperation with the engagement part of the dosing device or adaptor upon insertion of the cartridge.

7. A cartridge according to claim 6, wherein the or at least one of the engagement formations comprises a ramp formation for cooperation with the engagement part of the dosing device or adaptor, the ramp formation being configured to engage with the engagement part of the dosing device or adaptor upon insertion of the cartridge.

8. A cartridge according to claim 6, wherein the or at least one of the engagement formations comprises a recess for engagement with a corresponding projection of the dosing device or adaptor.

9. A cartridge according to claim 1, wherein the seal arrangement provides an enclosed chamber adjacent the sealing element for receiving a proximal tip of the release member when the seal is formed around the release member.

10. A cartridge according to claim 1, wherein the sealing element closes the passage.

11. A cartridge according to claim 1, wherein the sealing surface is defined by a narrowed region of the passage that is narrower than a remainder of the passage.

12. A cartridge according to claim 1, wherein the closure member comprises the seal arrangement.

13. A cartridge according to claim 12, wherein the closure member is elastically deformable to receive the release member and to form the seal around the release member.

14. A cartridge according to claim 1, wherein the coupling element comprises the seal arrangement.

15. A cartridge according to claim 14, wherein the seal arrangement comprises a tubular portion for receiving the release member.

16. A cartridge according to claim 15, wherein a proximal end of the tubular portion is arranged to clamp the closure member to the body.

17. A cartridge according to claim 14, wherein the closure member is an elastomeric disc.

18. A cartridge according to claim 1, wherein the closure member comprises an elastomeric bung which is at least partially received in the distal end of the cavity of the body.

19. A cartridge according to claim 1, wherein the distal end of the body comprises an annular collar, and wherein the coupling element includes a clip formation to engage with the collar, thereby to secure the coupling element to the body.

20. A cartridge according to claim 19, wherein the coupling element is arranged to apply a clamping force to the closure member when the clip formation is engaged with the collar, thereby to retain the closure member against the body.

21. A cartridge according to claim 19, comprising a retainer for applying a retaining force to the clip formation to maintain engagement between the clip formation and the collar.

22. A cartridge according to claim 1, wherein the sealing element comprises a pierceable septum.

23. A cartridge connector for a dosing device or adaptor for use with the cartridge of claim 1, comprising the engagement part for engagement with the coupling element of the cartridge to clip the cartridge to the dosing device or adaptor upon insertion of the cartridge to the cartridge connector.

24. A cartridge connector according to claim 23, wherein the engagement part is configured to engage with an engagement formation of the coupling element.

25. A cartridge connector according to claim 24, wherein the engagement part comprises a ramp formation for cooperation with the engagement formation of the coupling element of the cartridge.

26. A cartridge connector according to claim 25, wherein the ramp formation comprises a ramped proximal side to allow the engagement formation on the coupling element of the cartridge to pass the ramp formation upon insertion of the cartridge.

27. A dosing device comprising the cartridge connector according to claim 23 and a sealing element release member arranged to cooperate with the sealing element of the closure member upon insertion of the cartridge to allow release of medicament from the cartridge.

28. A dosing device according to claim 27, further comprising a cannula, wherein the release member comprises a tube member in fluid connection with the cannula.

29. A dosing device according to claim 28, wherein the tube member extends from an enlarged diameter part of the release member, and wherein the seal arrangement is arranged to form a seal with the enlarged diameter part of the release member.

30. A dosing device according to claim 28, wherein the cannula is non-axially aligned with respect to the release member.

31. A dosing device according to claim 27, further comprising a needle, wherein the release member comprises a proximal end of the needle.

32. An adaptor for use with the cartridge according to claim 1, the adaptor comprising:

the engagement part;

an adaptor body housing a medicament chamber;

an adaptor seal for sealing a distal end of the chamber; and wherein the sealing element release member is arranged to cooperate with the sealing element of the cartridge to allow flow of medicament from the cartridge to the chamber when the cartridge is clipped to the adaptor;

wherein the engagement part is arranged to engage with the coupling element of the cartridge to clip the cartridge to the adaptor.

33. An adaptor according to claim 32, wherein the sealing element release member comprises a tubular piercing member fluidly connected to the chamber.

34. An adaptor according to claim 32, comprising a cap fitting for securing the adaptor seal to the adaptor body.

35. An adaptor according to claim 34, wherein the cap fitting comprises a crimp closure and the adaptor body comprises a lip for retaining the closure.

36. An adaptor according to claim 32, wherein the adaptor body has an outer diameter that differs from an outer diameter of the coupling element of the cartridge.

37. An adaptor according to claim 32, further comprising attachment means for attachment of a disposable needle to the adaptor.

38. A medicament cartridge assembly comprising an adaptor according to claim 32 fitted to the cartridge.

* * * * *